(12) United States Patent
Warshel et al.

(10) Patent No.: US 8,855,936 B2
(45) Date of Patent: Oct. 7, 2014

(54) PRODUCTION OF STABLE PROTEINS

(75) Inventors: Arieh Warshel, Los Angeles, CA (US);
Spyridon Vicatos, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 932 days.

(21) Appl. No.: 12/896,781

(22) Filed: Oct. 1, 2010

(65) Prior Publication Data

US 2011/0082673 A1      Apr. 7, 2011

Related U.S. Application Data

(60) Provisional application No. 61/248,388, filed on Oct. 2, 2009.

(51) Int. Cl.
| | | |
|---|---|---|
| *G01N 33/48* | (2006.01) | |
| *G01N 33/50* | (2006.01) | |
| *G06F 19/16* | (2011.01) | |
| *G06F 19/12* | (2011.01) | |
| *G06F 19/10* | (2011.01) | |

(52) U.S. Cl.
CPC .............. *G06F 19/16* (2013.01); *G06F 19/12* (2013.01); *G06F 19/10* (2013.01)
USPC ........................................................ 702/19

(58) Field of Classification Search
CPC .......... G06F 19/10; G06F 19/12; G06F 19/16
See application file for complete search history.

(56) References Cited

PUBLICATIONS

Wang, "Can One Predict Protein Stability? An Attempt to Do So for Residue 133 of T4 Lysozyme Using a Combination of Free Energy Derivatives, PROFEC, and Free Energy Perturbation Methods," Proteins: Structure, Function, and Genetics, vol. 32, pp. 438-458, 1998.*
Alexandrova et al., (2008) "Catalytic mechanism and performance of computationally designed enzymes for Kemp elimination," J Am Chem Soc 130:15907-15.
Copeland et al., (1991) "The structure of human acidic fibroblast growth factor and its interaction with heparin," Arch Biochem Biophys, 289:53-61.
Creagh et al., (1998) "Stability and oligosaccharide binding of the N1 cellulose-binding domain of Cellulomonas fimi endoglucanase CenC," Biochemistry, 37:3529-37.
Cutler et al., (1989) "Role of arginine-38 in regulation of the cytochrome c oxidation-reduction equilibrium," Biochemistry, 28:3188-97.
Debler et al., (2005) "Structural origins of efficient proton abstraction from carbon by a catalytic antibody," Proc Natl Acad Sci U S A 102:4984-9.
Debler et al., (2009) "An aspartate and a water molecule mediate efficient acid-base catalysis in a tailored antibody pocket," Proc Natl Acad Sci U S A 106:18539-44.
Dryga et al., (2010) "Renormalizing SMD: the renormalization approach and its use in long time simulations and accelerated PMF calculations of macromolecules," J Phys Chem B. 114(39):12720-8.
Frushicheva et al., (2010) "Exploring challenges in rational enzyme design by simulating the catalysis in artificial kemp eliminase," Proc Natl Acad Sci U S A. 107(39):16869-74.
Gospodarowicz et al., (1986) "Heparin protects basic and acidic FGF from inactivation," J Cell Physiol, 128:475-84.
Grigorenko et al., (2005) "QM/MM Modeling the Ras-GAP Catalyzed Hydrolysis of Guanosine Triphosphate," Proteins 60:495-503.
Hollfelder et al., (2001) "On the magnitude and specificity of medium effects in enzyme-like catalysts for proton transfer," J Org Chem 66:5866-74.
Hwang et al., (1987) "Semiquantitative calculations of catalytic free energies in genetically modified enzymes," Biochemistry 26, 2669-73.
Kamerlin et al., (2010) "At the dawn of the 21st century: Is dynamics the missing link for understanding enzyme catalysis?" Proteins 78:1339-75.
Kamerlin et al., (2010) "On catalytic preorganization in oxyanion holes: highlighting the problems with the gas-phase modeling of oxyanion holes and illustrating the need for complete enzyme models," J Org Chem. 75(19):6391-401.
Kamerlin et al., (2010) "Examining the case for the effect of barrier compression on tunneling, vibrationally enhanced catalysis, catalytic entropy and related issues," FEBS Lett. 584(13):2759-66.
Kamerlin et al., (2010) "Ketosteroid isomerase provides further support for the idea that enzymes work by electrostatic preorganization," Proc Natl Acad Sci U S A. 107(9):4075-80.
Kamerlin et al., (2010) "Coarse-Grained (Multiscale) Simulations in Studies of Biophysical and Chemical Systems," Annu Rev Phys Chem. Apr. 2, 2010. [Epub ahead of print].
Kamerlin et al., (2009) "On the energetics of ATP hydrolysis in solution," J Phys Chem B. 113:15692-8.
Kemp et al., (1973) "Physical organic chemistry of benzisoxazoles II. Linearity of the bronsted free energy relationship for the base-catalyzed decomposition of benzisoxazoles," J. Am. Chem. Soc. 95:6670-80.
Khersonsky et al., (2010) "Evolutionary optimization of computationally designed enzymes: Kemp eliminases of the KE07 series," J Mol Biol 396, 1025-42.
Lee et al., (1993) "Microscopic and semimicroscopic calculations of electrostatic energies in proteins by the POLARIS and ENZYMIX programs," J Comp Chem. 14:161-85.

(Continued)

*Primary Examiner* — Michael Borin
(74) *Attorney, Agent, or Firm* — Foley & Lardner LLP; Antoinette F. Konski; Troy D. Smith

(57) ABSTRACT

The disclosure provides methods for designing and producing mutants that stabilize a protein. The folding energy of the protein and various mutants can be determined based on an equation comprising intrinsic $pK_a$, of the amino acids, the pH, charge of the amino acids, distances between the amino acids, an optimized dielectric constant for self-energy ($\in_p$) or an optimized dielectric constant for charge-charge interaction ($\in'_{\mathit{eff}}$) and compared. A more negative folding energy of the mutant indicates a more stable protein. When a stable mutant is identified, it can be produced with technologies such as cloning and expression.

6 Claims, 16 Drawing Sheets

(56) References Cited

PUBLICATIONS

Liu et al., (2007) "The Catalytic Effect od Dihydrofolate Reductase and Its Mutants Is Determined by Reorganization Energies," 46:6011-25.

Marti et al., (2007) "Computer-Aided Rational Design of Catalytic Antibodies: The 1F7 Case," Angewandte Chemie-International Edition 46:286-290.

Marti et al., (2008) "Predicting an Improvement of Secondary Catalytic Activity of Promiscuos Isochorismate Pyruvate Lyase by Computational Design," J. Am. Chem. Soc. 130:2894-5.

Messer et al., (2010) "Multiscale simulations of protein landscapes: using coarse-grained models as reference potentials to full explicit models," Proteins. 78(5):1212-27.

Muegge et al., (1998) "Electrostatic Contributions to Protein-Protein Binding Affinities: Application to Rap/Raf Interaction," Proteins 30:407-23.

Mulholland, AJ (2008) "Computational enzymology: modelling the mechanisms of biological catalysts," Biochemical Society Transactions 36:22-26.

Na et al., (1996) "Transition State of the Base-Promoted Ring-Opening of Isoxazoles. Theoretical Prediction of Catalytic Functionalities and Design of Haptens for Antibody Production," J Am Chem Soc 118:6462-71.

Nagel et al., (2009) "A 21st century revisionist's view at a turning point in enzymology," Nat Chem Biol. 5:543-50.

Olsson et al., (2004) "Solute solvent dynamics and energetics in enzyme catalysis: the S(N)2 reaction of dehalogenase as a general benchmark," J Am Chem Soc 126:15167-79.

Pace CN. (2000) "Single surface stabilizer," Nat Struct Biol. 7(5):345-6.

Reetz et al., (2006) "Iterative saturation mutagenesis on the basis of B factors as a strategy for increasing protein thermostability," Angew Chem Int Ed Engl. 45(46):7745-51.

Roca et al., (2007) "Electrostatic contributions to protein stability and folding energy," FEBS Lett. 581(10):2065-2071.

Roca et al., (2009) "Toward accurate screening in computer-aided enzyme design," Biochemistry 48:3046-56.

Rogers et al., (1974) "Synthesis and evaluation of a model for the so-called "charge-relay" system of the serine esterases," J Am Chem Soc 96, 2473-81.

Röthlisberger et al., (2008) "Kemp elimination catalysts by computational enzyme design," Nature 453:190-5.

Rychkova et al., (2010) "On the energetics of translocon-assisted insertion of charged transmembrane helices into membranes," Proc Natl Acad Sci U S A. 107(41):17598-603.

Schutz et al., (2001) "What are the dielectric 'constants' of proteins and how to validate electrostatic models," Proteins 44:400-17.

Sham et al., (1997) "Consistent calculations of pKa's of ionizable residues in proteins: Semi-microscopic and microscopic approaches," J Phys Chem B. 101(22):4458-72.

Sham et al., (1998) "The effect of protein relaxation on charge-charge interactions and dielectric constants of proteins," Biophys J. 74(4):1744-53.

Shan et al., (2008) "The low-pH unfolded state of the C-terminal domain of the ribosomal protein L9 contains significant secondary structure in the absence of denaturant but is no more compact than the low-pH urea unfolded state," Biochemistry 47(36):9565-73.

Sharma et al., (2007) "A new paradigm for electrostatic catalysis of radical reactions in vitamin B12 enzymes," Proc Natl Acad Sci U S A 104:9661-6.

Shurki et al., (2004) "Why does the Ras switch 'break' by oncogenic mutations?," Proteins 55:1-10.

Singh et al., (2010) "A comprehensive examination of the contributions to the binding entropy of protein-ligand complexes," Proteins 78(7):1724-35.

Singh et al., (2010) "Absolute binding free energy calculations: on the accuracy of computational scoring of protein-ligand interactions," Proteins. 78(7):1705-23.

Thorn et al., (1995) "Large rate accelerations in antibody catalysis by strategic use of haptenic charge," Nature 373:228-30.

Toscano et al., (2007) "Minimalist active-site redesign: Teaching old enzymes new tricks," Angewandte Chemie—International Edition 46:4468-70.

Trefethen JM (2005) "Charge-charge interactions in the denatured state influence the folding kinetics of ribonuclease Sa," Protein Sci. 14(7):1934-8.

Vicatos et al., (2009) "Effective Approach for Calculations of Absolute Stability of Proteins Using Focused dielectric Constants," Proteins 77:670-84.

Warshel et al., (2006) "Electrostatic basis for enzyme catalysis," Chem Rev 106:3210-35.

Warshel et al., (2006) "Modeling electrostatic effects in proteins," Biochim Biophys Acta. 1764(11):1647-76.

Warshel, A (1987) "What about protein polarity?," Nature 330:15-16.

Warshel et al., (1986) "Toward computer-aided site-directed mutagenesis of enzymes," Proc. Natl. Acad. Sci. USA 83:3806.

Wong et al., (2003) "Solution structure and thermal stability of ribosomal protein L30e from hyperthermophilic archaeon *Thermococcus celer*," Protein Sci. 12(7):1483-95.

Zhang (2008) "Progress and challenges in protein structure prediction," Curr Opin Struct Biol. 18(3):342-8.

\* cited by examiner

| e_p \ e_eff | 2.00 | 4.00 | 8.00 | 20.00 | 25.00 | 30.00 | 35.00 | 40.00 | 45.00 | 50.00 | 60.00 | 70.00 | 80.00 |
|---|---|---|---|---|---|---|---|---|---|---|---|---|---|
| 2.0 | -76.21 | -32.23 | -10.29 | 5.54 | 7.22 | 8.14 | 8.69 | 9.04 | 9.28 | 9.45 | 9.64 | 9.73 | 9.75 |
| 4.0 | -134.64 | -50.93 | -13.42 | 4.92 | 7.23 | 8.84 | 9.92 | 10.65 | 11.16 | 11.53 | 12.02 | 12.32 | 12.52 |
| 8.0 | -179.00 | -84.34 | -32.64 | -5.77 | -2.04 | 0.50 | 2.21 | 3.38 | 4.21 | 4.84 | 5.73 | 6.33 | 6.77 |
| 20.0 | -184.38 | -90.03 | -38.78 | -10.41 | -6.69 | -4.27 | -2.71 | -1.65 | -0.89 | -0.30 | 0.54 | 1.12 | 1.54 |
| 25.0 | -185.36 | -91.06 | -39.94 | -11.25 | -7.53 | -5.13 | -3.58 | -2.53 | -1.77 | -1.19 | -0.35 | 0.22 | 0.65 |
| 30.0 | -186.02 | -91.77 | -40.76 | -11.85 | -8.13 | -5.72 | -4.18 | -3.13 | -2.37 | -1.79 | -0.96 | -0.38 | 0.04 |
| 35.0 | -186.43 | -92.23 | -41.29 | -12.21 | -8.50 | -6.10 | -4.57 | -3.52 | -2.77 | -2.19 | -1.36 | -0.78 | -0.35 |
| 40.0 | -186.77 | -92.61 | -41.72 | -12.55 | -8.83 | -6.44 | -4.91 | -3.87 | -3.11 | -2.53 | -1.70 | -1.12 | -0.70 |
| 45.0 | -187.04 | -92.88 | -42.01 | -12.78 | -9.06 | -6.68 | -5.15 | -4.11 | -3.35 | -2.78 | -1.95 | -1.37 | -0.95 |
| 50.0 | -187.19 | -93.08 | -42.25 | -12.95 | -9.24 | -6.85 | -5.32 | -4.28 | -3.52 | -2.95 | -2.11 | -1.54 | -1.11 |
| 60.0 | -187.54 | -93.43 | -42.64 | -13.25 | -9.54 | -7.16 | -5.63 | -4.59 | -3.84 | -3.26 | -2.43 | -1.86 | -1.43 |
| 70.0 | -187.70 | -93.63 | -42.87 | -13.42 | -9.71 | -7.33 | -5.80 | -4.77 | -4.02 | -3.44 | -2.61 | -2.03 | -1.61 |
| 80.0 | -187.89 | -93.83 | -43.10 | -13.59 | -9.88 | -7.50 | -5.97 | -4.94 | -4.18 | -3.61 | -2.78 | -2.20 | -1.78 |

The best fitted region

FIG. 2

PRODUCTION OF STABLE PROTEINS

CROSS REFERENCE TO RELATED APPLICATION

This application claims the benefit under 35 U.S.C. §119(e) of U.S. Provisional Ser. No. 61/248,388, filed Oct. 2, 2009, the content of which is incorporated by reference in its entirety.

STATEMENT OF GOVERNMENT SUPPORT

This invention was made with government support under Grant No. GM24492 awarded by the National Institutes of Health. The U.S. Government has certain rights to the invention.

FIELD OF THE DISCLOSURE

The present invention generally relates to computer aided design of stable protein mutants and production of proteins with identified mutation that stabilizes the protein.

BACKGROUND

Throughout this disclosure, various technical and patent publications are referenced to more fully describe the state of the art to which this invention pertains. These publications are incorporated by reference, in their entirety, into this application.

Optimizing the stability of a given protein is one of the "holy grails" in many biotechnological and biochemical applications. Unfortunately it is extremely hard to predict the absolute stability of proteins and at present the most successful approaches are based on experimental search. Such approaches are obviously very time-consuming since they are based on experimental iterations. The development of a reliable computer-aided protein stabilization approach can be very helpful, but unfortunately none of the previous methods was able to provide a clear correlation between the absolute folding energy and the protein sequence. No computational method for automated sequence refinement has been reported.

The ability to predict physical and chemical properties of proteins, given their sequence and folded tertiary structure, is of crucial importance for the study of enzymes. Computational approaches for predicting the thermal stability of proteins, the difference of free energy between their folded and unfolded state, have yet to emerge and validate. That is, despite the progress in the development of models for studying the folding of proteins there are still major problems in predicting protein stability by either microscopic or macroscopic models. For example, there is a lack of a clear understanding of the magnitude of electrostatic contributions to thermal stability and to the overall folding free energy. Similarly, the values of the dielectric constants to be used and the contribution of the ionizable residues to the stability of a folded protein are only a few of the questions still unanswered.

Discretized continuum studies have suggested that charged and polar groups lead to destabilization of a folded protein. Other studies, however, have indicated that protein stability is far more complicated than originally thought, and that charged residues do not necessarily destabilize the protein core. Quite the opposite, they tend to increase protein stability. Even the general idea in continuum studies that internal ionizable residues tend to destabilize the protein core is now under reevaluation. Overall there is a growing realization that electrostatic energy is related to stability in general, and that electrostatic interactions usually stabilize the native states of proteins quite significantly.

However, the exact role of electrostatic interactions in protein stability is obscured by the competition between desolvation penalties, stabilization by local protein dipoles, and charge-charge interaction.

SUMMARY OF THE DISCLOSURE

The disclosure provides a method for producing a mutant of a protein that is more stable than the protein, comprising, or alternatively consisting essentially of, or alternatively consisting of:

a) determining the folding energy of the protein based on an equation comprising one or more parameters selected from the group of intrinsic $pK_a$ of one or more of the amino acids in the protein, the pH of a solution having the protein, charge of one or more amino acids in the protein, one or more distances between amino acids in the protein, an optimized dielectric constant for self-energy ($\in'_p$) or an optimized dielectric constant for charge-charge interaction ($\in'_{e\!f\!f}$);

b) identifying a mutation so that the folding energy of the protein having the mutation is more negative than the folding energy of the protein, wherein the folding energy is determined based on the equation; and c) producing a mutant of the protein including the mutation identified in step b).

In some embodiments, the method further comprises, or alternatively consisting essentially of, or alternatively consisting of, determining the sequence and/or structure of the protein before step a).

In some embodiments, the equation is:

$$\Delta G_{fold}^{elec} = \Delta G_{fold}^{elec}(\varepsilon'_p, \varepsilon'_{e\!f\!f})$$

$$\approx -2.3RT\sum_i Q_i(pK_{i,int}^p(\varepsilon'_p) - pK_{i,w}^w) +$$

$$166\sum_{i\neq j} Q_i Q_j \left[\frac{1}{r_{ij}^{(f)}\varepsilon_{e\!f\!f}^{\prime(f)}} - \frac{1}{80 r_{ij}^{(uf)}}\right]$$

wherein
  uf and f designate the unfolded and folded states respectively,
  $Q_i$ and $Q_j$ are the charges of the $i^{th}$ and $j^{th}$ residues respectively,
  $pK_{i,w}^w$ is the $pK_a$ of the $i^{th}$ residue in water,
  $PK_{i,int}^p$ ($\in'_p$) is the intrinsic $pK_a$ of the $i^{th}$ residue in its given protein state when all other residues are neutral, the notation $\in'_p$ indicating that this pKa is a function of $\in'_p$), and
  $r_{ij}$ is the distance between residues i and j.

In some embodiments, the equation is:

$$\Delta G_{fold}^{elec}(\varepsilon'_p, \varepsilon_{e\!f\!f}^{\prime(f)}) = -2.3RT\sum_i Q_i(pK_{i,int}^p(\varepsilon'_p) - pK_{i,w}^w) +$$

$$166\sum_{i\neq j} Q_i Q_j \left[\frac{1}{r_{ij}^{(f)}\varepsilon_{e\!f\!f}^{\prime(f)}}\right]$$

-continued $$= -2.3RT \sum_i Q_i(pK^p_{i,int}(\varepsilon'_p) - pK^w_{i,w}) + 166 \sum_{i \neq j} Q_i Q_j \left[\frac{1}{r_{ij}\varepsilon'_{eff}}\right].$$

The disclosure also provides a method for producing a mutant of a protein more stable than the protein, the mutant of the protein having substitute amino acid for one or amino acid residues, comprising, or alternatively consisting essentially of, or alternatively consisting of:

a) determining the change in charge ($\Delta Q_i$) for one or more amino acid residues in the protein;
b) identifying a substitute amino acid for each of the one or more amino acid residues, wherein the substitute amino acid is more positively charged than the amino acid residue if the change in charge ($\Delta Q_i$) is positive, or the substitute amino acid is more negatively charged than the amino acid residue if the change in charge ($\Delta Q_i$) is negative; and
c) producing a mutant of the protein including the one or more substitute amino acids identified in step b).

In some embodiments, the change in charge $\Delta Q_i$ is determined by:

$$\Delta Q_i = -\alpha \left(\frac{\partial \Delta G^{elec}_{fold}}{\partial Q_i}\right),$$

wherein the gradient of free energy over the charge of the protein is determined by:

$$\frac{\partial \Delta G^{elec}_{fold}}{\partial Q_i} \approx -2.3RT(pK^p_{i,int}(\varepsilon'_p) - pK^w_{i,w}) + 332 \sum_{i \neq j} Q_j \left[\frac{1}{r_{ij}(\varepsilon'_{eff})_{ij}}\right],$$

wherein α is a scaling factor,
($\in'_p$) is a dielectric constant for self-energy,
($\in'_{eff}$) is a dielectric constant for charge-charge interaction,
uf and f designate the unfolded and folded states respectively,
$Q_i$ and $Q_j$ are the charges of the $i^{th}$ and $j^{th}$ residues respectively,
$pK^w_{i,w}$ is the $pK_a$ of the $i^{th}$ residue in water,
$pK^p_{i,int}$ ($\in'_p$) is the intrinsic $pK_a$ of the $i^{th}$ residue in its given protein state when all other residues are neutral, the notation $\in'_p$ indicating that this pKa is a function of $\in'_p$), and
$r_{ij}$ is the distance between residues i and j.

The disclosure further provides computer aided methods for identifying amino acid substitutes and designing protein mutants that stabilize a protein.

In one aspect of any of the above embodiments of the disclosure, the $\in'_p$ is greater than about 35 and smaller than about 40, and/or the $\in'_{eff}$ is greater than about 35 and smaller than about 40.

BRIEF DESCRIPTION OF THE DRAWINGS

Provided embodiments are illustrated by way of example, and not limitation, in the figures of the accompanying drawings in which:

FIG. 2 shows the calculated values of $\Delta G_{fold}^{elec}$ as a function of $\in_p$ and $\in'_{eff}$ for L-Repressor, where the best fitted values of $\in'_p$ and $\in'_{eff}$ are taken as the values that give the best agreement between $\Delta G_{fold}^{elec}(\in'_p,\in'_{eff})$ and the observed $\Delta G_{fold}$ and observed stability for this protein is −4.6 kcal/mole (as seen from the figure, these values are around $35 \leq \in'_p \leq 45$ and $35 \leq \in'_{eff} \leq 45$);

FIG. 3 also shows that the calculated best fitted values of $\Delta G_{fold}^{elec}(\in'_p,\in'_{eff})$ diverge greatly from the corresponding observed values and the average error between observed $\Delta G_{fold}$ and best fitted $\Delta G_{fold}^{elec}(\in'_p,\in'_{eff})$ is 3.5 kcal/mole, and 7.3 kcal/mole for (A) and (B), respectively (some points of (B) are outside the scale of this figure);

FIG. 7 shows the best fitted $\Delta G_{fold}^{elec}(\in'_p,\in'_{eff})$ and observed $\Delta G_{fold}$ for the tested proteins, after the use of lower $\in'_p$ for the internal residues and lower $\in'_{eff}$ for the Lys with $r_{ij} \leq 10$ Å; FIG. 7 further shows that In this case, all proteins show best fitted values of $\Delta G_{fold}^{elec}(\in'_p,\in'_{eff})$ when dielectric constants are in the range of $35 \leq \in'_p \leq 40$ and $35 \leq \in'_{eff} \leq 40$ and the difference between best fitted $\Delta G_{fold}^{elec}(\in'_p,\in'_{eff})$ and observed $\Delta G_{fold}$ has significantly decreased, compared to the previous cases of FIGS. 3 and 5 (for 45 proteins, the average difference is reduced to 0.7 kcal/mole);

Figure 1:
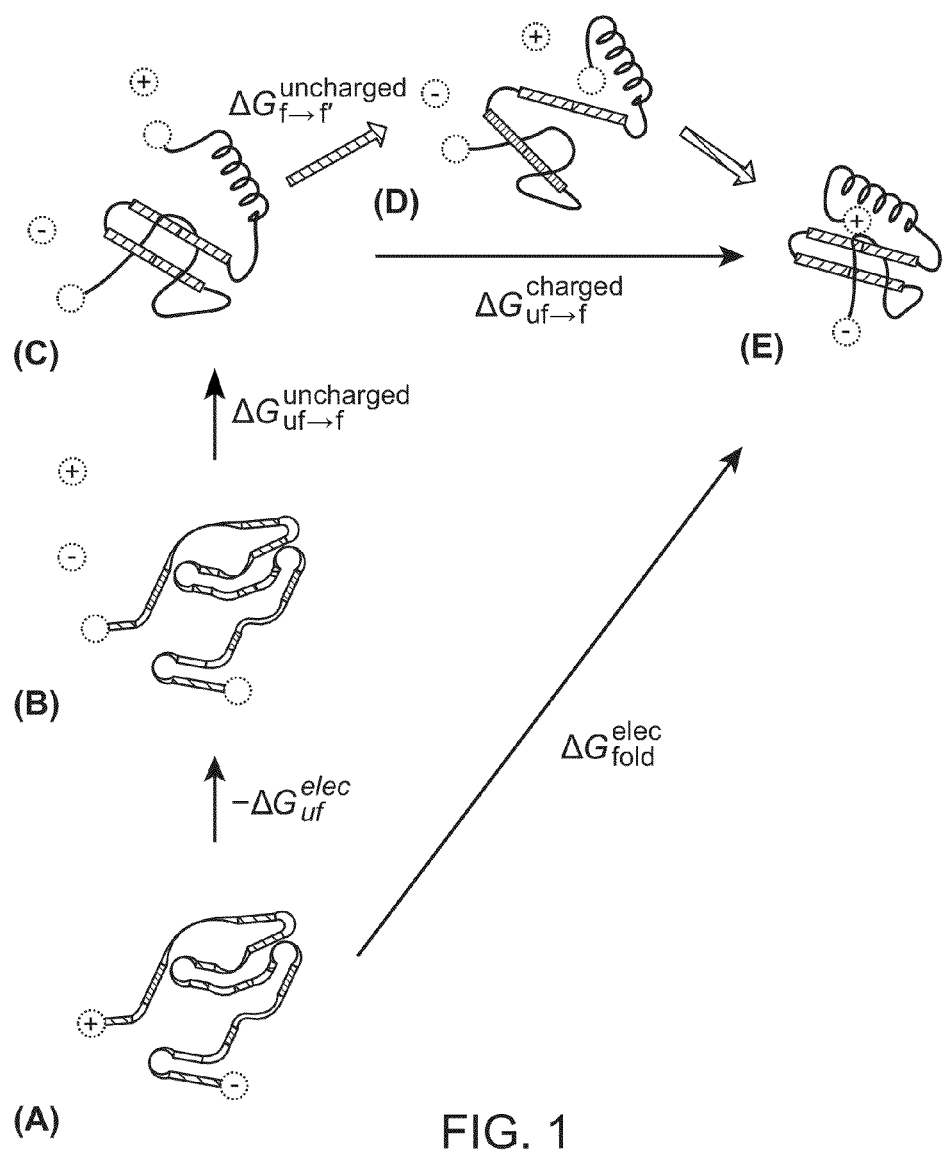
FIG. 1 shows the thermodynamic cycle for the folding of a charged protein. Steps A->B and B->C correspond, respectively, to the uncharging of the unfolded protein and the folding of the uncharged protein, where step C->D corresponds to the change of the unfolded protein from its equilibrium structure to the structure of the folded charged protein, step A->E corresponds to a direct folding of the ionized protein and the figure defines the free energy terms used in this application.

It will be recognized that some or all of the figures are schematic representations for purposes of illustration and do not necessarily depict the actual relative sizes or locations of the elements shown. The figures are provided for the purpose of illustrating one or more embodiments with the explicit understanding that they will not be used to limit the scope or the meaning of the claims.

Detailed Description of the Disclosure

Throughout this disclosure, various publications, patents and published patent specifications are referenced by an identifying citation. The disclosures of these publications, patents and published patent specifications are hereby incorporated by reference in their entirety into the present disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

As used herein, certain terms have the following defined meanings. Terms that are not defined have their art recognized meanings.

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements that would materially affect the basic and novel characteristics of the disclosure. "Consisting of" shall mean excluding any element, step, or ingredient not specified in the claim. Embodiments defined by each of these transition terms are within the scope of this disclosure.

A "processor" is an electronic circuit that can execute computer programs. Examples of processors include, but are not limited to, central processing units, microprocessors, graphics processing units, physics processing units, digital signal processors, network processors, front end processors, coprocessors, data processors and audio processors.

A "memory" refers to an electrical device that stores data for retrieval. In one aspect, a memory is a computer unit that preserves data and assists computation.

A "storage medium" or "data storage device" refers to a device for recording information. Recording can be done using virtually any form of energy, spanning from manual muscle power in handwriting, to acoustic vibrations in phonographic recording, to electromagnetic energy modulating magnetic tape and optical discs. In one aspect, a storage medium is a computer hard drive. In another aspect, a storage medium is a computer memory. In yet another aspect, a storage medium is a flash drive for a portable or wireless computing device.

The terms "nucleic acid", "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, small interference RNA (siRNA), double strand RNA (dsRNA), ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

A "mutation" or mutant refers to a change to the nucleotide sequence of the genetic material of an organism, or the amino acid sequence of a protein or polypeptide.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells, or alternatively from a prokaryotic cells as described above. Non-limiting examples include simian, bovine, porcine, murine, rats, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus bacteria, E. coli* bacterium, and *Salmonella* bacterium.

Protein Production and Sequence and Structure Determination

Protein Production

Protein expression is a subcomponent of gene expression. It consists of the stages after DNA has been translated into polypeptide chains, which are ultimately folded into proteins. Protein expression is commonly used by proteomics researchers to denote the measurement of the presence and abundance of one or more proteins in a particular cell or tissue.

Proteins can be expressed in various expression systems, including in vivo, in vivo or in cell free systems. An expression host can be prokaryotic or eukaryotic. An expression system is a system specifically designed for the production of a gene product of choice. An expression system consists of a gene, normally encoded by DNA, and the molecular machinery required to transcribe the DNA into mRNA and translate the mRNA into protein using the reagents provided. In the broadest sense this includes every living cell but the term is more normally used to refer to expression as a laboratory tool. An expression system is therefore often artificial in some manner. Viruses are an excellent example where they replicate by using the host cell as an expression system for the viral proteins and genome.

The oldest and most widely used expression systems are cell-based and may be defined as the "combination of an expression vector, its cloned DNA, and the host for the vector that provide a context to allow foreign gene function in a host cell, that is, produce proteins at a high level". Expression is often done to a very high level and therefore referred to as overexpression.

There are many ways to introduce foreign DNA to a cell for expression, and there are many different host cells which may be used for expression—each expression system has distinct advantages and liabilities. Expression systems are normally referred to by the host and the DNA source or the delivery mechanism for the genetic material. For example, common hosts are bacteria (such as *E. coli, B. subtilis*), yeast (such as *S. cerevisiae*) or eukaryotic cell lines. Common DNA sources and delivery mechanisms are or viruses (such as baculovirus, retrovirus, adenovirus), plasmids, artificial chromosomes and bacteriophage (such as lambda). The best expression system of choice depends on the gene involved, for example the *Saccharomyces cerevisiae* is often preferred for proteins that require significant posttranslational modification and Insect or mammal cell lines are used when human-like splicing of the mRNA is required. Nonetheless, bacterial expression has the advantage of easily producing large amounts of protein, which is required for X-ray crystallography or nuclear magnetic resonance experiments for structure determination.

*E. coli* is one of the most popular hosts for artificial gene expression. *E. coli* is one of the most widely used expression hosts, and DNA is normally introduced in a plasmid expression vector. The techniques for overexpression in *E. coli* are well developed and work by increasing the number of copies of the gene or increasing the binding strength of the promoter region so assisting transcription.

For example a DNA sequence for a protein of interest could be cloned or subcloned into a high copy-number plasmid containing the lac promoter, which is then transformed into the bacterium *Escherichia coli*. Addition of IPTG (a lactose analog) activates the lac promoter and causes the bacteria to express the protein of interest.

Cell-free expression of proteins is possible using purified RNA polymerase, ribosomes, tRNA and ribonucleotides. These reagents may be produced by extraction from cells or from a cell-based expression system. Due to the low expression levels and high cost of cell-free systems cell-based systems are more widely used.

Other expression systems, such as algae and plant, have also been widely used.

Mutagenesis

A mutant protein can be generated by methods known in the art, and typically through expression of a polynucleotide encoding the mutated protein. Non-limiting examples of methods to generate a mutant polynucleotide include PCR mutagenesis, transposon mutagenesis, site-directed mutagenesis, directed mutagenesis, insertional mutagenesis and targeted mutagenesis.

Protein Sequence and Structure Determination

Protein sequence can be determined directly or through sequencing of the polynucleotide/DNA encoding it. Methods for performing protein sequencing include, for example, Edman degradation, peptide mass fingerprinting, mass spectrometry, and protease digests.

Protein structures can be determined by methods known in the art, including but not limited to, X-ray crystallography and Nuclear Magnetic Resonance (NMR). Around 90% of the protein structures available in the Protein Data Bank have been determined by X-ray crystallography. This method allows one to measure the 3D density distribution of electrons in the protein (in the crystallized state) and thereby infer the 3D coordinates of all the atoms to be determined to a certain resolution.

Roughly 9% of the known protein structures have been obtained by Nuclear Magnetic Resonance techniques, which can also be used to determine secondary structure. Note that aspects of the secondary structure as whole can be determined via other biochemical techniques such as circular dichroism or dual polarisation interferometry. Secondary structure can also be predicted with a high degree of accuracy. Cryo-electron microscopy has recently become a means of determining protein structures to high resolution (less than 5 angstroms or 0.5 nanometer) and is anticipated to increase in power as a tool for high resolution work in the next decade. This technique is still a valuable resource for researchers working with very large protein complexes such as virus coat proteins and amyloid fibers.

A number of methods for the computational prediction of protein structure from its sequence have been proposed. Ab initio prediction methods use just the sequence of the protein. Threading uses existing protein structures. Homology Modeling to build a reliable 3D model for a protein of unknown structure from one or more related proteins of known structure. The recent progress and challenges in protein structure prediction was reviewed by Zhang (Zhang (2008) Curr. Opin. Struct. Biol. 18(3):342-348).

Details of the Disclosure

The disclosure provides methods of identifying amino acid substitutes and designing protein mutants that stabilize a protein, and also provides methods to produce such stable proteins.

In one aspect, the disclosure provides a method for determining the folding energy of a protein in a custom computing apparatus, the custom computing apparatus comprising at least one processor and a memory, the method comprising, or alternatively consisting essentially of, or alternatively consisting of:

receiving, in the memory, a plurality of parameters comprising one or more selected from the group of intrinsic $pK_a$ of one or more of the amino acids in the protein, the pH of a solution having the protein, charge of one or more amino acids in the protein, one or more distances between amino acids in the protein, an optimized dielectric constant for self-energy ($\in'_p$) or an optimized dielectric constant for charge-charge interaction ($\in'_{eff}$);

accessing, by the at least one processor the plurality of parameters; and calculating, by the at least one processor, based on an equation for the folding energy of the protein, the plurality of parameters being inputs to the equation.

Another aspect of the disclosure provides a method for identifying a mutation of a protein that stabilizes the protein in a custom computing apparatus, wherein the custom computing apparatus comprises at least one processor and a memory, wherein the method comprises:

receiving, in the memory, a first set of parameters comprising one or more selected from the group of intrinsic $pk_a$ of one or more of the amino acids in the protein, the pH of a solution having the protein, charge of one or more amino acids in the protein, one or more distances between amino acids in the protein, an optimized dielectric constant for self-energy ($\in'_p$) or an optimized dielectric constant for charge-charge interaction ($\in'_{eff}$);

accessing, by the at least one processor the first set of parameters;

calculating, by the at least one processor, based on an equation for the folding energy of the protein, the plurality of parameters being inputs to the equation;

receiving, in the memory, a second set of parameters comprising one or more selected from the group of intrinsic $pK_a$ of one or more of the amino acids in the protein having the mutation, the pH of a solution having the protein having the mutation, charge of one or more amino acids in the protein having the mutation, one or more distances between amino acids in the protein having the mutation, an optimized dielectric constant for self-energy ($\in'_p$) or an optimized dielectric constant for charge-charge interaction ($\in'_{eff}$);

accessing, by the at least one processor the second set of parameters; and calculating, by the at least one processor, based on an equation for the folding energy of the protein having the mutation, the plurality of parameters being inputs to the equation, wherein that the folding energy of the protein having the mutation is more negative than the folding energy of the protein not having the mutation identifies that the mutation stabilizes the protein.

The disclosure, in yet another aspect, provides a custom computing apparatus comprising, or alternatively consisting essentially of, or alternatively consisting of:

at least one processor;

a memory coupled to the at least one processor;

a storage medium in communication with the memory and the at least one processor, wherein the storage medium contains a set of processor executable instructions that, when executed by the processor configure the custom computing apparatus to determine the folding energy of a protein, wherein instructions configure the apparatus to:

receive, in the memory, a plurality of parameters comprising one or more selected from the group of intrinsic $pK_a$ of one or more of the amino acids in the protein, the pH of a solution having the protein, charge of one or more amino acids in the protein, one or more distances between amino acids in the protein, an optimized dielectric constant for self-energy interaction ($\in'_p$) or an optimized dielectric constant for charge-charge interaction ($\in'_{eff}$);

access, by the at least one processor the plurality of parameters; and calculate, by the at least one processor, based on an equation for the folding energy of the protein, the plurality of parameters being inputs to the equation.

Also provided in the disclosure is a custom computing apparatus comprising, or alternatively consisting essentially of, or alternatively consisting of:

at least one processor;

a memory coupled to the at least one processor;

a storage medium in communication with the memory and the at least one processor, wherein the storage medium contains a set of processor executable instructions that, when executed by the processor configure the custom computing apparatus to identify a mutation of a protein that stabilizes a protein, wherein instructions configure the apparatus to:

receive, in the memory, a first set of parameters comprising one or more selected from the group of intrinsic $pK_a$ of one or more of the amino acids in the protein, the pH of a solution having the protein, charge of one or more amino acids in the protein, one or more distances between amino acids in the protein, an optimized dielectric constant for self-energy ($\in'_p$) or an optimized dielectric constant for charge-charge interaction ($\in'_{eff}$);

access, by the at least one processor the first set of parameters;

calculate, by the at least one processor, based on an equation for the folding energy of the protein, the plurality of parameters being inputs to the equation;

receive, in the memory, a second set of parameters comprising one or more selected from the group of intrinsic $pK_a$ of one or more of the amino acids in the protein having the mutation, the pH of a solution having the protein having the mutation, charge of one or more amino acids in the protein having the mutation, one or more distances between amino acids in the protein having the mutation, an optimized dielectric constant for self-energy ($\in'_p$) or an optimized dielectric constant for charge-charge interaction ($\in'_{eff}$);

access, by the at least one processor the second set of parameters; and calculate, by the at least one processor, based on an equation for the folding energy of the protein having the mutation, the plurality of parameters being inputs to the equation, wherein that the folding energy of the protein having the mutation is more negative than the folding energy of the protein not having the mutation identifies that the mutation stabilizes the protein.

Figure 10:
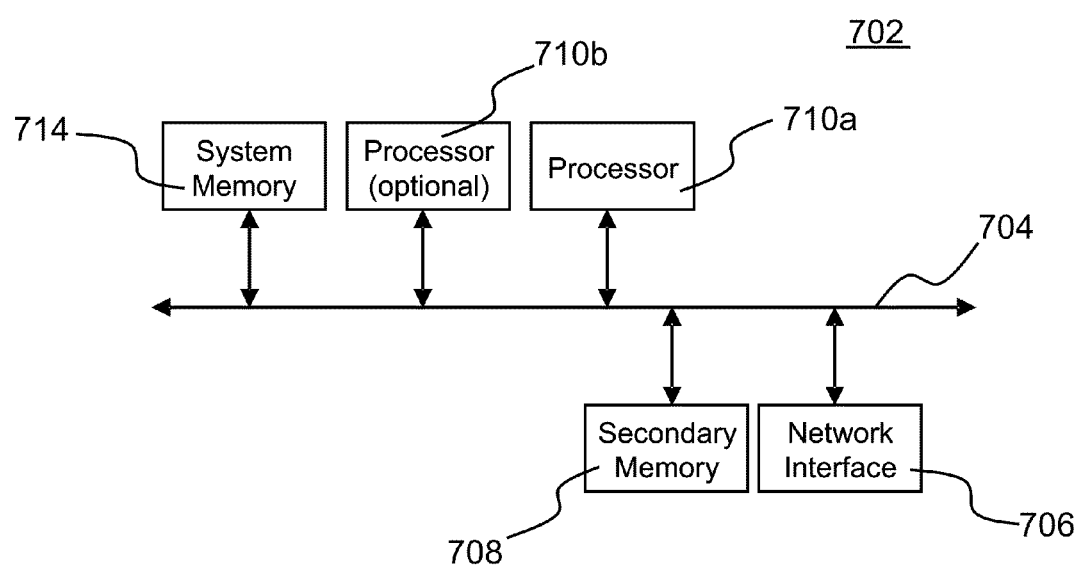
FIG. 10 shows exemplary computer system suitable for use with the present disclosure.

Computational apparatuses and devices, including processors, memories and storages have been well described in art. An exemplary computational device is illustrated in FIG. 10. Computational operations, including data access, data processing and calculation etc are known to those skilled in the art.

Another aspect of the disclosure provides a method for producing a mutant of a protein that is more stable than the protein, comprising, or alternatively consisting essentially of, or alternatively consisting of:

a) determining the folding energy of the protein based on an equation comprising one or more parameters selected from the group of intrinsic $pK_a$ of one or more of the amino acids in the protein, the pH of a solution having the protein, charge of one or more amino acids in the protein, one or more distances between amino acids in the protein, an optimized dielectric constant for self-energy ($\in'_p$) or an optimized dielectric constant for charge-charge interaction ($\in'_{eff}$);

b) identifying a mutation so that the folding energy of the protein having the mutation is more negative than the folding energy of the protein, wherein the folding energy is determined based on the equation; and c) producing a mutant of the protein including the mutation identified in step b).

In some embodiments, the further comprising determining the sequence and/or structure of the protein before step a). This is useful for designing stable mutations for proteins, of which sequence or structure is not known. Methods for determining the sequence or structure of a protein is known in the art and is briefly described herein.

In one aspect of any of the above embodiments of methods, the equation is:

$$\Delta G^{elec}_{fold} = \Delta G^{elec}_{fold}(\varepsilon'_p, \varepsilon'_{eff})$$

$$\approx -2.3RT \sum_i Q_i(pK^p_{i,int}(\varepsilon'_p) - pK^w_{i,w}) +$$

$$166 \sum_{i \neq j} Q_i Q_j \left[ \frac{1}{r^{(f)}_{ij} \varepsilon'^{(f)}_{eff}} - \frac{1}{80 r^{(uf)}_{ij}} \right]$$

wherein
uf and f designate the unfolded and folded states respectively,
$Q_i$ and $Q_j$ are the charges of the $i^{th}$ and $j^{th}$ residues respectively,
$pK_{i,w}^w$ is the $pK_a$ of the $i^{th}$ residue in water,
$pK_{i,int}^p$ is the intrinsic $pK_a$ of the $i^{th}$ residue in its given protein state when all other residues are neutral, the notation $\in_p$ that this pKa is a function of $\in_p$), and
$r_{ij}$ is the distance between residues i and j.

In another aspect of any of the above embodiments of methods, the equation is:

$$\Delta G^{elec}_{fold}(\varepsilon'_p, \varepsilon'^{(f)}_{eff}) = -2.3RT \sum_i Q_i(pK^p_{i,int}(\varepsilon'_p) - pK^w_{i,w}) +$$

$$166 \sum_{i \neq j} Q_i Q_j \left[ \frac{1}{r^{(f)}_{ij} \varepsilon'^{(f)}_{eff}} \right]$$

$$= -2.3RT \sum_i Q_i(pK^p_{i,int}(\varepsilon'_p) - pK^w_{i,w}) +$$

$$166 \sum_{i \neq j} Q_i Q_j \left[ \frac{1}{r_{ij} \varepsilon'_{eff}} \right]$$

wherein
uf and f designate the unfolded and folded states respectively, $Q_i$ and $Q_j$ are the charges of the $i^{th}$ and $j^{th}$ residues respectively, $pK_{i,w}{}^w$ is the $pK_a$ of the $i^{th}$ residue in water, $pK_{i,int}{}^p$ ($\in'_p$) is the intrinsic $pK_a$ of the $i^{th}$ residue in its given protein state when all other residues are neutral, the notation $\in'_p$ indicating that this pKa is a function of $\in'_p$), and $r_{ij}$ is the distance between residues i and j.

In one aspect of any of the above embodiments of the methods, the $\in'_p$ is greater than about 5, or alternatively about 10, or about 15, or about 20, or about 25, or about 30, or about 35 or about 40. In another aspect, the $\in'_p$ is smaller than about 60, or alternatively about 55, or about 50, or about 45, or about 40, or about 35, or about 30. In one aspect, the $\in'_{eff}$ is greater than about 5, or alternatively about 10, or about 15, or about 20, or about 25, or about 30, or about 35 or about 40. In another aspect, the $\in'_{eff}$ is smaller than about 60, or alternatively about 55, or about 50, or about 45, or about 40, or about 35, or about 30. In a particular aspect of any of the above embodiments of the methods, the $\in'_p$ is greater than about 35 and smaller than about 40. In yet another aspect, the $\in'_{eff}$ is greater than about 35 and smaller than about 40.

Yet further provides is a method for producing a mutant of a protein more stable than the protein, the mutant of the protein having substitute amino acid for one or amino acid residues, comprising, or alternatively consisting essentially of, or alternatively consisting of:

a) determining the change in charge ($\Delta Q_i$) for one or more amino acid residues in the protein;

b) identifying a substitute amino acid for each of the one or more amino acid residues, wherein the substitute amino acid is more positively charged than the amino acid residue if the change in charge ($\Delta Q_i$) is positive, or the substitute amino acid is more negatively charged than the amino acid residue if the change in charge ($\Delta Q_i$) is negative; and c) producing a mutant of the protein including the one or more substitute amino acids identified in step b).

In one aspect, the change in charge $\Delta Q_i$ is determined by:

$$\Delta Q_i = -\alpha \left( \frac{\partial \Delta G^{elec}_{fold}}{\partial Q_i} \right),$$

wherein the gradient of free energy over the charge of the protein is determined by:

$$\frac{\partial \Delta G^{elec}_{fold}}{\partial Q_i} \approx -2.3RT(pK^p_{i,int}(\varepsilon'_p) - pK^w_{i,w}) + 332 \sum_{i \neq j} Q_j \left[ \frac{1}{r_{ij}(\varepsilon'_{eff})_{ij}} \right],$$

wherein α is a scaling factor, ($\in'_p$) is a dielectric constant for self-energy, ($\in'_{eff}$) is a dielectric constant for charge-charge interaction, uf and f designate the unfolded and folded states respectively, $Q_i$ and $Q_j$ are the charges of the $i^{th}$ and $j^{th}$ residues respectively, $pK_{i,w}{}^w$ is the $pK_a$ of the $i^{th}$ residue in water, $pK_{i,int}{}^p$ ($\in'_p$) is the intrinsic $pK_a$ of the $i^{th}$ residue in its given protein state when all other residues are neutral, the notation $\in'_p$ indicating that this pKa is a function of $\in'_p$), and $r_{ij}$ is the distance between residues i and j.

In one aspect, the $\in'_p$ is greater than about 35 and smaller than about 40. In another aspect, the $\in'_{eff}$ is greater than about 35 and smaller than about 40.

Still further provided is a method for identifying a substitute amino acid at each of one or more amino acid residues of a protein that stabilizes the protein in a custom computing apparatus, wherein the custom computing apparatus comprises at least one processor and a memory, wherein the mutant of the protein has substitute amino acid at one or more amino acid residues, the method comprising, or alternatively consisting essentially of, or alternatively consisting of:

receiving, in the memory, a first set of parameters comprising one or more selected from the group of intrinsic $pK_a$ of one or more of the amino acids in the protein, the pH of a solution having the protein, charge of one or more amino acids in the protein, one or more distances between amino acids in the protein, a dielectric constant for self-energy ($\in'_p$) or a dielectric constant for charge-charge interaction ($\in'_{eff}$);

accessing, by the at least one processor the first set of parameters; and calculating, by the at least one processor, based on an equation for the change in charge ($\Delta Q_i$) of one or more amino acid residues of the protein, the plurality of parameters being inputs to the equation, wherein a positive change in charge ($\Delta Q_i$) indicates the substitute amino acid should be more positively charged than the amino acid residue, or a negative change in charge ($\Delta Q_i$) indicates the substitute amino acid should be more negatively charged than the amino acid residue.

In one aspect, the change in charge $\Delta Q_i$ is determined by the equation:

$$\Delta Q_i = -\alpha \left( \frac{\partial \Delta G^{elec}_{fold}}{\partial Q_i} \right),$$

wherein the gradient of free energy over the charge of the protein is determined by:

$$\frac{\partial \Delta G^{elec}_{fold}}{\partial Q_i} \approx -2.3RT(pK^p_{i,int}(\varepsilon'_p) - pK^w_{i,w}) + 332 \sum_{i \neq j} Q_j \left[ \frac{1}{r_{ij}(\varepsilon'_{eff})_{ij}} \right],$$

wherein α is a scaling factor, ($\in'_p$) is a dielectric constant for self-energy, ($\in'_{eff}$) is a dielectric constant for charge-charge interaction, uf and f designate the unfolded and folded states respectively, $Q_i$ and $Q_j$ are the charges of the $i^{th}$ and $j^{th}$ residues respectively, $pK_{i,w}{}^w$ is the $pK_a$ of the $i^{th}$ residue in water, $pK_{i,int}{}^p$ ($\in'_p$) is the intrinsic $pK_a$ of the $i^{th}$ residue in its given protein state when all other residues are neutral, the notation $\in'_p$ indicating that this pKa is a function of $\in'_p$), and $r_{ij}$ is the distance between residues i and j.

Determining mutations that would lead to the largest stability of the given protein can be done using the gradient of the folding free energy with respect to the charge of each of the protein residues. The gradient provides the predicted change in charge ($\Delta Q_i$) for each residue. When the predicted change of charge is positive, it means that changing the protein residue to a more positively charged residue, e.g., changing to a positively charged residue if the original residue is neutral, or changing to a neutral residue if the original residue is negatively charged, will increase the protein stability. If the predicted charge in change ($\Delta Q_i$) is negative it means that changing the residue to a more negatively charged residue, e.g., changing to a negative residue if the original residue is neutral, or changing to a neutral residue if the original residue is positively charged, will increase the protein stability.

In one aspect, the $\in'_p$ is greater than about 35 and smaller than about 40. In another aspect, the $\in'_{eff}$ is greater than about 35 and smaller than about 40.

In some embodiments of any of the above methods, the steps in the methods can be repeated for a finite number of iterations, each of which iterations may result in identification of mutations or amino acid substitutions that further stabilize the protein. Ultimately, a protein mutation can be identified and produced that maximally stabilize the protein.

The following examples are provided to illustrate certain aspects of the present disclosure and to aid those of skill in the art in practicing the disclosure. These examples are in no way to be considered to limit the scope of the disclosure.

EXAMPLE 1

This example provides a general and automated computational way for stabilizing proteins by using optimal mutations. The method is based on using a general expression for the free energy of folding, $\Delta G_{fold}$ (where specific "focused" dielectric constants are employed) and on an iterative optimization of the protein sequence. The method provides a powerful, cost/energy-efficient, quick to produce results tool for protein design.

The method described here is the first, computer based method, which predicts the effects of mutations on $\Delta G_{fold}$ of a protein, and its absolute stability of folding $\Delta G_{fold}$. Furthermore, this example provides an automated iterative search for the sequence that would give the maximum stability to the given protein. This method is the first computational method that can accurately predict $\Delta G_{fold}$ and its dependence upon mutations. More importantly, the iterative optimization approach provides the first effective computer based stabilization method.

The method uses the idea of specially optimized dielectric constants for self-energy and charge-charge interactions ($\in'_p$ and $\in'_{eff}$ respectively) and can provide a reliable function that estimates the absolute folding free energy. With this in mind the gradient of the folding free energy with regards to the charges of the protein residues $$\left(\frac{\partial \Delta G_{fold}}{\partial Q_i}\right)$$

are evaluated and searched for the optimum of the folding energy. The use of the current approach appeared to be surprisingly effective, first in terms of predicting observed folding energies (FIG. 7) and second in being able to predict the sequence that would lead to the most stable calculated structure and also to the reproduction of the observed stability starting from a less stable sequence.

An article published by the applicants, Vicatos et al. (2009) Proteins: Structure, Function, and Bioinformatics 77:670-684, further fully describes the method. The content of the article is incorporated into the current disclosure by reference in its entirety.

I. Method

The method described in this example focuses on the electrostatic contribution to the folding free energy, assuming that this is the main contribution.

The starting point is the folding paths of FIG. 1, where the system can move from the unfolded state (A) to the folded state (E) in two pathways. In one of them (A)→(B)→(C)→(D)→(E), the unfolded protein becomes uncharged (transferring the charges to solution on the proper proton transfer process), folds to its neutral folded form (C), and then move to the final folded charged form (E) through an uncharged structure that is similar to that of (E). In the second path the charged protein folds directly by moving from (A) to (E). The electrostatic contributions to folding, $\Delta G_{fold}^{elec}$, of a given protein at a specific ionization state and at a given pH, is evaluated by (Warshel et al. (2006) Biochim. Biophys. Acta. 1764(11):1647-1676):

$$\Delta G_{fold}^{elec} = \Delta G_f^{elec} - \Delta G_{uf}^{elec} \qquad (1)$$

$$= -2.3RT \sum_i Q_i^{(f)}(pK_{i,int}^p(\varepsilon_p) - pH) +$$

$$166 \sum_{i \neq j} \frac{Q_i^{(f)} Q_j^{(f)}}{r_{ij}^{(f)} \varepsilon_{eff}(r_{ij}^{(f)})} + 2.3RT \sum_i Q_i^{(uf)}(pK_{a,i}^w - pH) -$$

$$166 \sum_{i \neq j} \frac{Q_i^{(uf)} Q_j^{(uf)}}{\varepsilon_{water} r_{ij}^{(uf)}}$$

where uf and f designate, the unfolded and folded states, $Q_i$ is the charge of the $i^{th}$ residue, in the folding (f) or the unfolding (uf) state, $\in_p$ is the dielectric constant used in the semimacroscopic calculation of intrinsic $pK_a$, $pK_{i,int}^p(\in_p)$ is the intrinsic $pK_a$ of the $i^{th}$ residue in its given protein state when all other residues are neutral, at a given $\in_p$. Finally $r_{ij}$ is the distance between residues i and j, while $\in_{eff}$ is the effective dielectric for charge-charge interactions inside the protein and $\in_{water}$ is the effective dielectric constant for charge-charge interactions in water.

As clarified elsewhere (Warshel et al. (2006) Biochim. Biophys. Acta. 1764(11):1647-1676 and Schutz and Warshel (2001) Proteins 44:400-417), $\in_p$ determines the intrinsic $pK_a$ and represents the "self energy" of each charged group. This parameter is not related to the response of the protein to electric field but to the method used in the calculations and to the elements included in the simulation system. Basically, $\in_p$ reflects all the effects that are not included explicitly in the given model (Schutz and Warshel (2001) Proteins 44:400-417). On the other hand, $\in_{eff}$ is a phenomenological parameter that represents the free energy of charge-charge interactions. This parameter reflects the compensation of the gas phase charge-charge interaction by the reorganization of the solvent and the protein.

The folding free energy also includes non electrostatic contributions such as configuration entropy and hydrophobic contributions. These contributions depend on the path used in FIG. 1. For example, according to FIG. 1, $$\Delta G_{fold} = \Delta G_f^{elec} - \Delta G_{uf}^{elec} + \Delta G_{uf \to f}^{uncharged} = \Delta G_{fold}^{elec} + \Delta G_{uf \to f}^{uncharged} \qquad (2)$$

In this description the electrostatic terms represent the charging process in the folded state and the uncharging in the unfolded state, while the non electrostatic is entirely associated with the folding of the fully uncharged protein. The use of this equation for mutations of ionized residues of a given protein allows one to focus only on $\Delta G_{fold}^{elec}$.

Now, Eq. 1 describes the electrostatic contribution to the folding energy of a protein, and the corresponding value depends upon the choice of $\in_p$ and $\in_{eff}$. Concerning the non electrostatic term $\Delta G_{uf \to f}^{uncharged}$, it can have different value for different proteins, and there is no current computational method that can guarantee its evaluation. However, if one uses the direct (A)→(E) path of FIG. 1 one can get a different picture to calculate $\Delta G_{fold}$ since now the entire folding process can be described as an electrostatic process where, $$\Delta G_{fold} \cong 166 \sum_{i \neq j} \frac{Q_i Q_j}{\varepsilon_{eff}(r_{ij})} \left[ \frac{1}{r_{ij}^{(f)}} - \frac{1}{r_{ij}^{(uf)}} \right] \quad (3)$$

That is, now the non electrostatic effects may be absorbed in the effective dielectric for bringing the charged groups from the unfolded to the folded state in the (A)→(E) path of FIG. 1. That is, the step (B)→(D) involves non-electrostatic contributions that may be significant, while the step (D)→(E) is formally a well defined electrostatic step, which includes structural reorganization. The dielectric that reflects the structural reorganization in the (D)→(E) step can be modified by considering the free energy of the (B)→(D) step (requiring that this free energy will be reproduced by Eq. 1). Now if the effect of the (B)→(D) step is not large or if it is correlated with the trend in the electrostatic free energy, one will have a uniform dielectric that works for all proteins. Conversely if this is not the case one will not be able to use such approximation. It is this approach, though with some assumptions, that leads to the next important step of the current method. The concept of a dielectric constant is further clarified in Warshel et al. (2006) Biochim. Biophys. Acta. 1764(11): 1647-1676, Schutz and Warshel (2001) Proteins 44:400-417 and Sham et al. (1998) Biophys. J. 74(4):1744-1753.

If the $\Delta G_{uf \to f}^{uncharged}$ term is small and the compensation between the entropy and the hydrophobic effect, one may examine the approximation:

$$\Delta G_{fold} \approx \Delta G_{fold}^{elec}(\in'_p, \in'_{eff}) \quad (4)$$

where $(\in'_p, \in'_{eff})$ is the set of $\in_p$ and $\in_{eff}$ that successfully reproduce the folding energy. In this case the following is obtained:

$$\Delta G_{fold}^{elec} = \Delta G_{fold}^{elec}(\varepsilon'_p, \varepsilon'_{eff}) \quad (5)$$

$$\approx -2.3RT \sum_i Q_i(pK_{i,int}^p(\varepsilon'_p) - pK_{i,w}^w) +$$

$$166 \sum_{i \neq j} Q_i Q_j \left[ \frac{1}{r_{ij}^{(f)} \varepsilon_{eff}^{'(f)}} - \frac{1}{80 r_{ij}^{(uf)}} \right]$$

Where: uf and f designate, the unfolded and folded states, $Q_i$ is the charge of the $i^{th}$ residue, in the folding (f) state only, $pK_{i,int}^p(\in'_p)$ is the intrinsic $pK_a$ of the $i^{th}$ residue calculated from the chosen $\in'_p$ and not the original $\in_p$, and $pK_{i,w}^w$ is the $pK_a$ of the i residue in water. Rigorously, one should use $Q^{(f)}$ but since the contribution from the unfolded state is neglected that leaves the notation $Q_i$. Eighty was also instead of the $\in_{water}$ since the difference is trivial and the effect of this term is small. Finally, $r_{ij}$ is the distance between residues i and j, in the folding (f) and unfolding (uf) state. Here $\in_{eff}^{'(f)}$ is the chosen dielectric effective constant for the charge-charge interactions. It should be pointed out that $\in_{eff}^{'(f)}$ in Eq. 5 is taken here as independent of the distance $r_{ij}$. In sections of Vicatos et al. (2009) Proteins: Structure, Function, and Bioinformatics 77:670-684, exceptions are discussed, where the choice of $\in_{eff}^{'(f)}$ for certain cases is affected by both the residues i and j as well as its distance $r_{ij}$.

Thus, the complicated and difficult problem of calculating absolute folding energy of a protein can be reduced to the finding of the proper, (optimal) values of $\in'_p$ and $\in'_{eff}^{(f)}$, which correctly calculate $\Delta G_{fold}$. This idea is based on the fact that semimacroscopic models can represent implicitly physical and chemical properties even though they lack explicit representation of the phenomena taking place. Such an approach can work only if the given model retains the main physics of the real system. In the current model, it is expected that the optimal values of and $\in'_p$ and $\in'_{eff}^{(f)}$ are higher than the values of 4 to 8, values used for example to calculate accurate values of $pK_a$'s in proteins (Sham et al. (1997) J. Phys. Chem. B 101(22):4458-4472).

Eq. 5 can be further simplified, by assuming that $r_{ij}^{(uf)}$ is in general much larger than $r_{ij}^{(f)}$, and that $\in_{eff}^{'(f)}$ is smaller than 80. Thus, Eq. 5 takes its final form, used in this work:

$$\Delta G_{fold}^{elec}(\varepsilon'_p, \varepsilon_{eff}^{'(f)}) = -2.3RT \sum_i Q_i(pK_{i,int}^p(\varepsilon'_p) - pK_{i,w}^w) + \quad (6)$$

$$166 \sum_{i \neq j} Q_i Q_j \left[ \frac{1}{r_{ij}^{(f)} \varepsilon_{eff}^{'(f)}} \right]$$

$$= -2.3RT \sum_i Q_i(pK_{i,int}^p(\varepsilon'_p) - pK_{i,w}^w) +$$

$$166 \sum_{i \neq j} Q_i Q_j \left[ \frac{1}{r_{ij} \varepsilon'_{eff}} \right]$$

In Equation 6 when dropping the notation (f) from the variables $r_{ij}^{(f)}$, $\in_{eff}^{'(f)}$, one will use $r_{ij}$, $\in'_{eff}$ as the distance and the corresponding charge-charge interaction dielectric constant for two residues i and j in the folding state. This simplification may overlook cases where the contribution from the unfolded protein is significant. This might be the case when the unfolded protein has a compact structure, as implied by the studies of Raleigh and coworkers (Shan et al. (2008) Biochemistry 47(36):9565-9573) or when electrostatic interaction in the unfolded state play a significant role for folding kinetics as suggested by Pace, Trefethen and coworkers (Pace (2000) Nat. Struct. Biol. 7(5):345-346 and Trefethen et al. (2005) Protein Sci. 14(7):1934-1938). However it is possible that the contribution from the unfolded configuration might still be relatively small and the best way to judge the issue is to explore the validity of Eq. 6 on a large number of test cases.

The computationally most intensive part of this model is the calculations of the intrinsic $pK_a$'s. This can be done by using the PDLD/S-LRA method according to standard protocol using the POLARIS module and the ENZYMIX force field of MOLARIS program (Roca et al. (2007) FEBS Lett. 581(10):2065-2071 and Wong et al. (2003) Protein Sci. 12(7): 1483-1495). It can also be done in principle by other programs that evaluate reliably electrostatic energies. The intrinsic $pK_a$'s for all ionizable residues, $pK_{i,int}^p(\in'_p)$, is evaluated by the PDLD/S-LRA and the ionization states of the protein residues at pH=7 are determined, by using a Monte Carlo approach described previously (Lee et al. (1993) J. Comp. Chem. 14:161-185). This procedure is repeated at different $\in'_p$, $\in'_{eff}$ and provides the charges (the $Q_i$) of the ionized residues as a function of the given dielectric constants. Using the $pK_{i,int}^{p}(\in'_p)$ and the $Q_i$ in Eq. 6 provides $\Delta G_{fold}^{elec}(\in'_p, \in'_{eff})$ as a function of $\in'_p$ and $\in'_{eff}$. It is important, in the above step, to use optimal values of the two dielectric constants, but even the use of a single high dielectric constant is envision in the current approach as a reasonable strategy.

II. Results

Initial Estimate of the Best Fitted Values of $\in'_P$ and $\in'$hd eff

In this example, all the proteins listed in Table I were considered. This test set included 45 proteins with various sequence sizes, folds, and function.

In order to clarify the nature of FIG. 1, it is useful to start, for example, with the evaluation of $\Delta G_{fold}^{elec}(\in'_p, \in'_{eff})$ at a specific point (e.g., $\in'_p=20$ and $\in'_{eff}=30$). In this case, the test first used $\in'_p=20$ and evaluate the intrinsic $pK_a$ values for all the ionizable residues. In the next step, the test used Eq. (6) with $\in'_{eff}=30$ and obtained $\Delta G_{fold}^{elec}(\in'_p, \in'_{eff}) = \Delta G_{fold}^{elec}(20,30) = -4.27$ kcal/mol. This value was then assigned in the corresponding point in FIG. 1. Now the same procedure was repeated for other values of $\in'_p$ and $\in'_{eff}$ and the figure was completed. Next, the test identified the set of $\Delta G_{fold}^{elec}(\in'_p, \in'_{eff})$ that gave the best agreement with the observed $\Delta G_{fold}$ (around 24.6 kcal/mole for L-Repressor) and identified the optimal dielectric constants. In the case of FIG. 2, the best fitted values were found to be in the vicinity $\in'_p = \in'_{eff} = 40$.

After applying the above approach to all the 45 proteins of the test case, this test considered several alternative ways of

TABLE I

Proteins tested in Example 1

| No. | Name | PDB ID | Number of residues | Type | Source |
|---|---|---|---|---|---|
| 1 | SSO7d | 1SSO | 62 | monomer | 37 |
| 2 | Thioredoxin | 2TRX | 108 | monomer | 37 |
| 3 | Barstar | 1A19 | 89 | monomer | 37 |
| 4 | Apoflavodoxin | 1FTG | 168 | monomer | 37 |
| 5 | λ-Repressor | 1LMB | 87 | monomer | 37 |
| 6 | Snase | 1EY0 | 136 | monomer | 37 |
| 7 | BsHpr, Phosphotransferase | 2HID | 87 | monomer | 37 |
| 8 | FeCyt $b_{562}$ | 1QPU | 106 | monomer | 37, 38 |
| 9 | Arc Repressor | 1ARQ | 53 | dimer | 37, 39 |
| 10 | Aspartate Amilotransferase | 1VPE | 398 | monomer | 3 |
| 11 | Chey | 1TMY | 118 | monomer | 3 |
| 12 | GDH Domain II | 1B26 (A02) | 234 | monomer | 2, 3, 37 |
| 13 | Histidine Phosphocarrier | 1Y4Y | 87 | monomer | 3 |
| 14 | Phosphotransferase, Histidine containing protein | 2HPR | 87 | monomer | 3 |
| 15 | Ribosomal | 1H7M | 99 | monomer | 34 |
| 16 | RNase H* | 1JXB | 147 | monomer | 3, 40 |
| 17 | Ferridoxin | 1VJW | 59 | monomer | 3 |
| 18 | O-Methyl Guanine DNA methyltransferase | 1MGT | 169 | monomer | 3 |
| 19 | Sac7d | 1WD0 | 66 | monomer | 2, 3 |
| 20 | $^a$Histone | 1BFM | 134 | dimer | 2, 41 |
| 21 | PFRD-XC4 | 1QCV | 53 | monomer | 42 |
| 22 | $^a$Staphylococcal Nuclease I92K | 1TR5 | 130 | monomer | 43 |
| 23 | Staphylococcal Nuclease I92E | 1TR5 | 130 | monomer | 43 |
| 24 | $^a$Staphylococcal Nuclease | 1TR5 | 130 | monomer | 43 |
| 25 | Bs CSP | 1CSP | 67 | monomer | 20, 44 |
| 26 | Bc CSP | 1C9O | 66 | monomer | 20, 45 |
| 27 | Tm CSP | 1G6P | 61 | monomer | 2, 20 |
| 28 | $^a$Ubiquitin D21N | 1AAR | 76 | monomer | 20, 46 |
| 29 | Ubiquitin F45W | 1AAR | 76 | monomer | 20, 47 |
| 30 | $^a$Ubiquitin K27A | 1AAR | 76 | monomer | 20, 46 |
| 31 | Tm DHFR | 1CZ3 | 164 | dimer | 20, 48 |
| 32 | Ec DHFR | 1RX2 | 159 | monomer | 20 |
| 33 | Ribonuclease | 1X1P | 212 | monomer | 2, 49 |
| 34 | Glucanase C | 1CX1 | 153 | monomer | 50 |
| 35 | Phospholipid A2 | 1P2P | 124 | monomer | 51 |
| 36 | Trypsin Proteinase | 2CI2 | 65 | monomer | 52 |
| 37 | Interleukin | 1IOB | 153 | monomer | 53 |
| 38 | $^a$Adhesion transferase Y92E | 1K40 | 126 | monomer | 54 |
| 39 | Complement | 1GKG | 136 | monomer | 4 |
| 40 | Cytochrome b5 Rat | 1B5M | 84 | monomer | 55 |
| 41 | Gene V DNA Binding | 1VQB | 86 | monomer | 56 |
| 42 | Glu Transferase | 1GSD | 208 | dimer | 57 |
| 43 | Growth Factor | 1FGA | 124 | monomer | 58 |
| 44 | Isomerase | 1HTI | 248 | dimer | 59 |
| 45 | Ribosomal S6 | 1RIS | 97 | dimer | 60 |

$^a$The structure used to calculate the $\Delta G_{fold}^{elec}$ was obtained by mutating the corresponding PDB structure reported in the third column of this table.

The test started with a rough estimate of the best fitted set of $\in'_p$ and $\in'_{eff}$ for the prediction of $\Delta G_{fold}$. This was done first for a single protein (L-Repressor, PDB ID 1 LMB) by the approach illustrated in FIG. 1.

analyzing the corresponding results. The first and simplest analysis which is summarized in FIG. 3, was based on allowing both $\in'_p$ and $\in'_{eff}$ to be either 35 or 40, and choosing the value of $\Delta G_{fold}^{elec}(\in'_p, \in'_{eff})$ that minimizes the difference $|\Delta G_{fold}^{elec}(\in'_p, \in'_{eff}) - \Delta G_{fold}^{obs}|$. The corresponding results were used to generate FIG. 3(A). This type of treatment will be referred here as getting the "best fitted" $\Delta G_{fold}^{elec}(\in'_p, \in'_{eff})$. The same procedure was followed in the generation of FIG. 3(B), but this time with $8 \leq \in'_p \leq 20$ and $8 \leq \in'_{eff} \leq 20$.

As seen from both FIGS. 3(A) and 3(B), there is significant disagreement between the best fitted $\Delta G_{fold}^{elec}(\in'_p, \in'_{eff})$ and observed $\Delta G_{fold}$ for many proteins. However, from these initial trials it appears that with the use of high values of $\in'_p$ and $\in'_{eff}$ of around 40, the absolute difference between observed and calculated stability $|\Delta G_{fold}^{elec}(\in'_p, \in'_{eff}) - \Delta G_{fold}|$ is significantly smaller than the difference obtained with other dielectric constants (see example demonstrated in FIG. 3(B), where the discrepancy is much larger at the region when $8 \leq \in'_p \leq 20$ and $8 \leq \in'_{eff} \leq 20$).

Improving the Model

In the next stage of the refinement of the model, this example tried to further search for the best fitted values for the dielectric constants. This was done by considering the dielectrics that minimize the function $$F_{error}(\varepsilon'_p, \varepsilon'_{eff}) = \sum_i |\Delta G_{(i)fold}^{elec}(\varepsilon'_p, \varepsilon'_{eff}) - \Delta G_{(i)fold}^{obs}| \quad (7)$$

where i runs on all 45 test proteins, and $F_{error}(\in'_p, \in'_{eff})$ is the sum of the absolute value of errors between calculated and observed stabilities, for a specific value of $\in'_p$ and $e\in'_{eff}$. The resulting surface is shown in FIGS. 4(A) and 4(B).

As seen from the figures, the best fitted values of $\in'_p$ and $\in'_{eff}$ follow approximately a line where $\in'_p = \in'_{eff}$, and the global minimum occurs approximately where $\in'_p = \in'_{eff} = 40$. Thus, it is concluded that the best fitted dielectrics needed for prediction of protein stability is the one around $\in'_p = \in'_{eff} = 40$.

Figure 3:
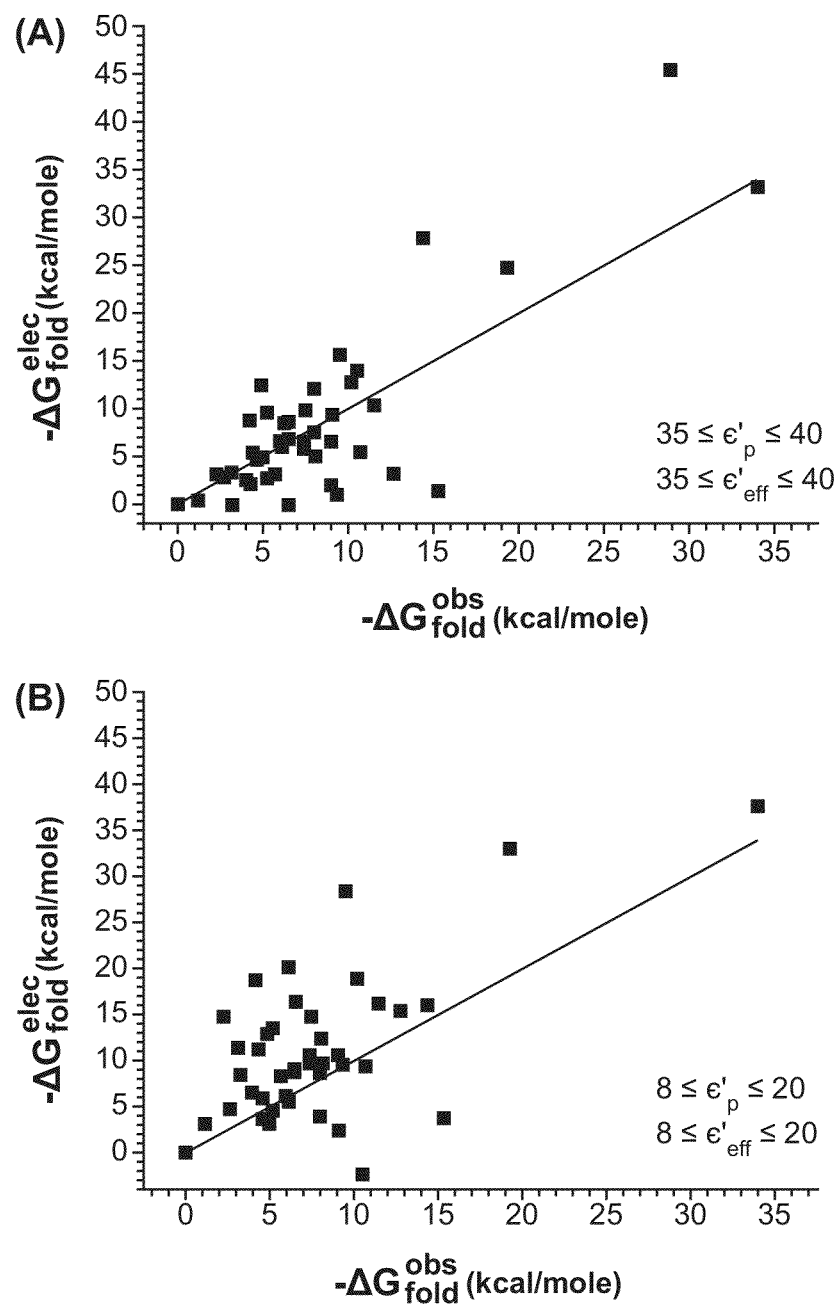
FIG. 3 shows the correlation between the best fitted $\Delta G_{fold}^{elec}(\in'_p,\in'_{eff})$ and $\Delta G_{fold}$ for best fitted values of $\in'_p$ and $\in'_{eff}$ in a restricted range. The calculations considered all the proteins in the benchmark of Table I and take the value of $\Delta G_{fold}^{elec}(\in'_p,\in'_{eff})$ that gives best fitted results for the two allowed values of $\in'_p$ and $\in'_{eff}$, where the two values considered in (A) are $\in'_p, \in'_{eff}=35, 40$ whereas in (B) $\in'_p, \in'_{eff}=8, 20$.
Figure 5:
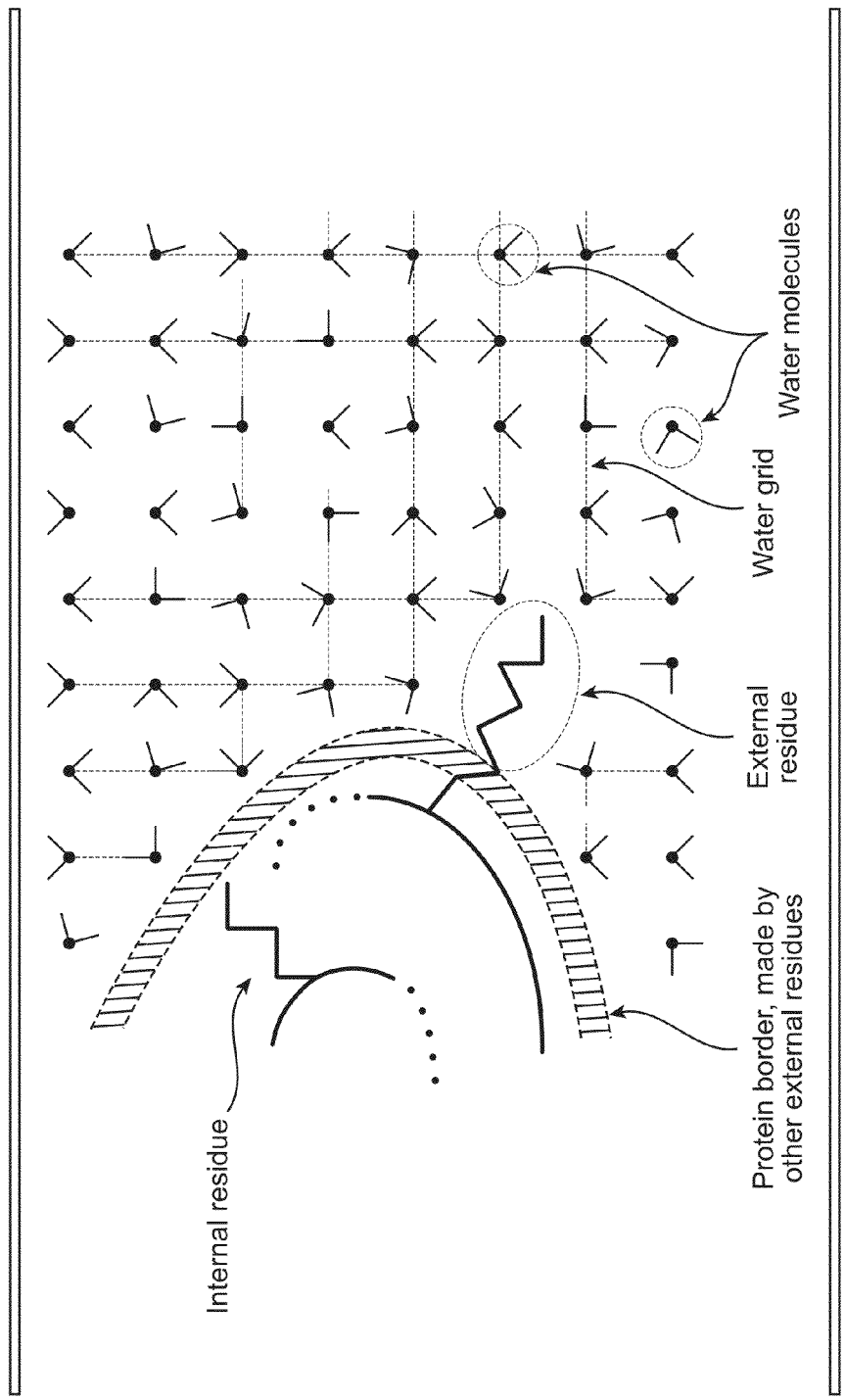
FIG. 5 illustrates the procedure for defining internal groups, where the protein is surrounded by a cubic grid of water molecules and the distance between the water oxygen and the given group is used to determine whether the group is internal or external.

To improve the performance of the model, this example started with a global analysis of the reasons for the disagreement between the calculated and observed values shown in FIG. 3. This analysis focused first on the location of the ionized residues in the cases that have not produced satisfactory results. This was done by evaluating the distance between the ionized groups to the closest water molecule using the grid created by MOLARIS in the initial process of generating the SCAAS water. The use of water grid in the identification of the internal/external residues is illustrated in FIG. 5.

The above grid analysis indicated that the main problem is associated with internal groups, and led to modify the approach, with the working hypothesis that in the case of truly internal groups it is better to use lower $\in'_p$ while still using a large $\in'_{eff}$. This was done by defining an internal residue when the following conditions occur: (a) the shortest distance between a grid point and a heavy atom of the given residue is higher or equal to the threshold value reported in Table II, depending upon the type of the residue, and (b) the given residue has a low number of water molecules within a radius of 5 (five or less water molecules) from its geometrical center. Condition (b) was used mainly as a verification of condition (a).

TABLE II

The threshold distances between the terminal heavy atom of the given amino acid and the closest grid point (the closest water molecule)

| Residue type | Threshold (Å) |
|---|---|
| ASP | 5.0 |
| GLU | 5.2 |
| HIS | 5.2 |
| LYS | 5.5 |
| ARG | 5.7 |

For example, a Glu residue is considered to be internal when there are five or less water molecules within a distance of 5 Å from its geometrical center, and the closest water is 5.2 Å or more from its furthest heavy atom, which in this case is one of the two oxygen atoms off its side chain.

If a single ionizable residue is identified as an internal residue, then the intrinsic $pK_a$ for this residue is chosen to take a value between the calculated $pK_{i,int}^p$ for $\in'_p = 8$ and the $pK_{i,int}^p$ for $\in'_p = 20$. For example, if a tested protein has 20 ionizable residues, and residue 17 is identified as internal, then in Eq. (6), for residue i=17 the $pK_a$ value used will be:

$$pK_{17,int}^p(\varepsilon'_p = \text{fixed}) \cong \frac{pK_{17,int}^p(\varepsilon'_p = 8) + pK_{17,int}^p(\varepsilon'_p = 20)}{2} \quad (8)$$

Now Eq. (6) for this case (protein with 20 ionizable residues and one internal residue) becomes:

$$\Delta G_{fold}^{elec}(\varepsilon'_p, \varepsilon'_{eff}) = -2.3RT \sum_{\substack{i=0 \\ i \neq 17}}^{20} Q_i(pK_{i,int}^p(\varepsilon'_p) - pK_{i,w}^w) - \qquad (9)$$

$$2.3RTQ_{17}(pK_{17,int}^p(\varepsilon'_p = \text{fixed}) - pK_{17,w}^w) + 166 \sum_{i \neq j} Q_iQ_j \left[\frac{1}{r_{ij}\varepsilon'_{eff}}\right]$$

In some cases this example identified internal ionizable residues with a very large difference between calculated $pK_{i,int}^p(\in'_p)$ and $pK_{i,w}^w$. In these cases this example found it useful to use an even lower value of $\in'_p$. Thus this example further refined the procedure and used an intrinsic $pK_a$ subscript that corresponds to $\in'_p = 8$ when the difference $pK_{i,int}^p(\in'_p) - pK_{i,w}^w$ for values of $\in'_p$ between 4 and 8 was positive and higher than 4 for Asp and Glu, and negative and lower than 23 for Lys and Arg.

Figure 6:
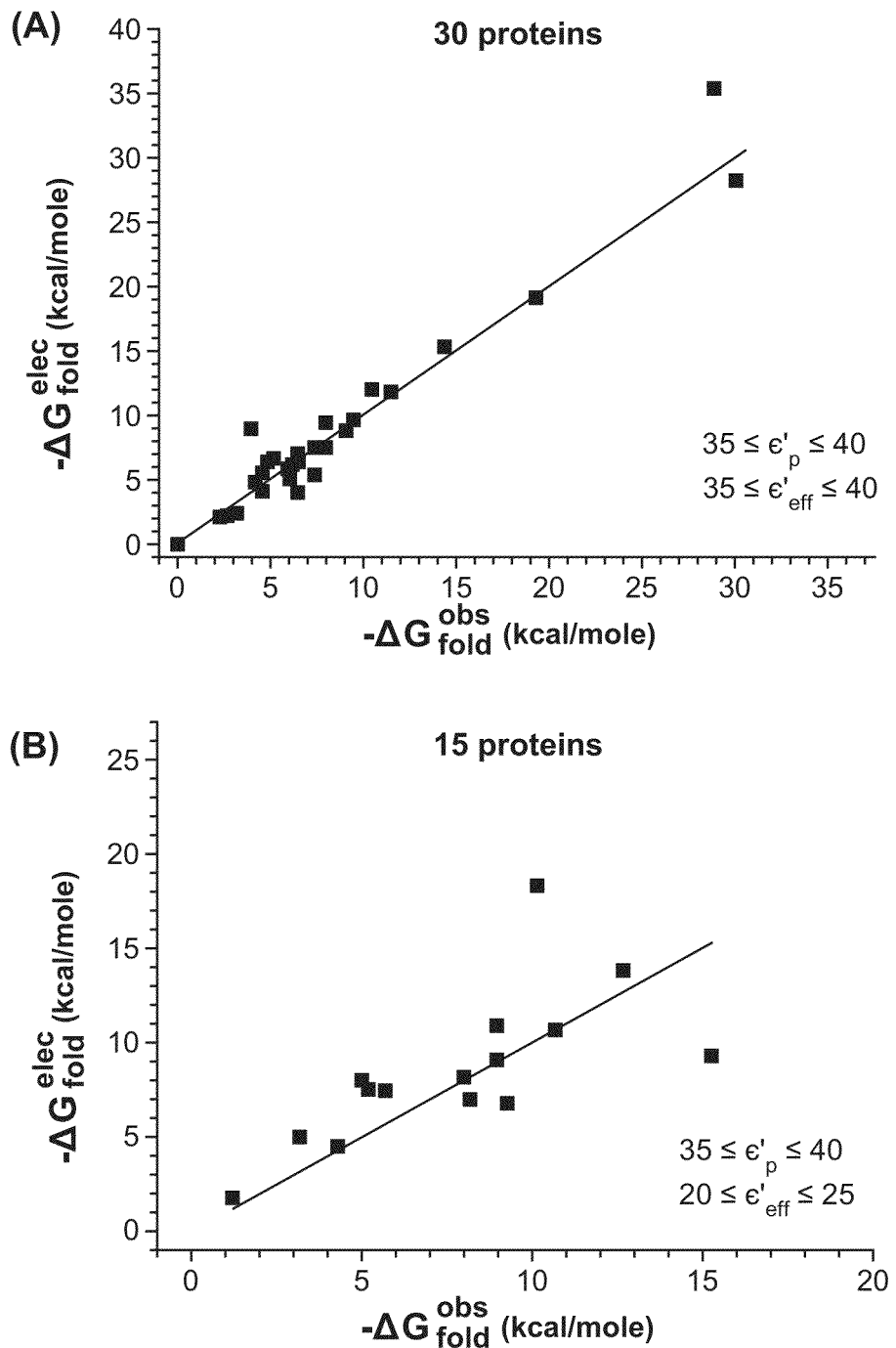
FIG. 6A-B are scatter plots showing the correlation between $\Delta G_{fold}^{elec}$ and $\Delta G_{fold}^{obs}$ after using lower $\in'_p$ for the internal residues; Both (A) and (B) use the same representation as in FIG. 3 and show that the test proteins fall into two main categories: (a) the one shown in (A) where the best fitted $\Delta G_{fold}^{elec}(\in'_p,\in'_{eff})$ is in the range of $35 \leq \in'_p \leq 40$ and $35 \leq \in'_{eff} \leq 40$, and (b) the one shown in (B) where the best fitted $\Delta G_{fold}^{elec}(\in'_p,\in'_{eff})$ is in the range $35 \leq \in'_p \leq 40$ and $20 \leq \in'_{eff} \leq 25$ wherein the majority of the test proteins fall into the first category.

Assigning lower $\in'_p$ values and using the corresponding $pK_{i,int}^p(\in'_p)$ for the internal ionizable residues, resulted in a significant increase in the accuracy of the calculated $\Delta G_{fold}$ for the protein test set. Now the majority of the proteins were showing excellent $\Delta G_{fold}$ predictions for dielectrics of $\in'_p = \in'_{eff} = 40$. However, this example also observed that a significant fraction of the tested proteins give more accurate results for $30 \leq \in'_p \leq 40$ and $20 \leq \in'_{eff} \leq 25$. The result for both cases are shown in FIGS. 6(A) and 6(B), respectively.

Some of the results obtained after the specialized treatment of the internal residues were still puzzling. That is, although the majority of the proteins tests were giving excellent results for $\in'_p = \in'_{eff} = 40$, there was still a significant number of proteins where $\Delta G_{fold}^{elec}(\in'_p, \in'_{eff})$ was substantially lower than $\Delta G_{fold}$, (see FIG. 6B). However, the fact that in both cases the value of $\in'_p$ was around 40 indicated that the problem is due to $\in'_{eff}$ that produced—in certain cases—the underestimation of $\Delta G_{fold}$. To decipher this non obvious behavior of $\in'_{eff}$, this example concentrated on proteins cases where point mutation resulted in "shifting" the best fitted values of $\in'_p$ and $\in'_{eff}$ from the $35 \leq \in'_p \leq 40$ and $35 \leq \in'_{eff} \leq 40$ range to the $35 \leq \in'_p \leq 40$ and $20 \leq \in'_{eff} \leq 25$ range, and vice versa. This was found in the case of the CSP where this example examined three proteins with high sequence similarities and only a few point mutations. In the case of bs-CSP this example obtained the best results in the $35 \leq \in'_p \leq 40$ and $20 \leq \in'_{eff} \leq 25$ range, in the case of bc-CSP this example obtained the best results in the $35 \leq \in'_p \leq 40$ and $25 \leq \in'_{eff} \leq 30$ range, while in the case of tm-CSP this example obtained the best results in the $35 \leq \in'_p \leq 40$ and $35 \leq \in'_{eff} \leq 40$ range. The analysis of this data indicated that the interaction of Lys residue with charged residues at 10 Å or less leads to the above shift. Thus, this example modified the $\in'_{eff}$ for the interaction of Lys with negatively charged residues by using:

$$(\in'_{eff})_{shift} = 0.8 \in'_{eff} \quad (10)$$

for a distance $r_{ij} \leq 10$ Å.

Figure 7:
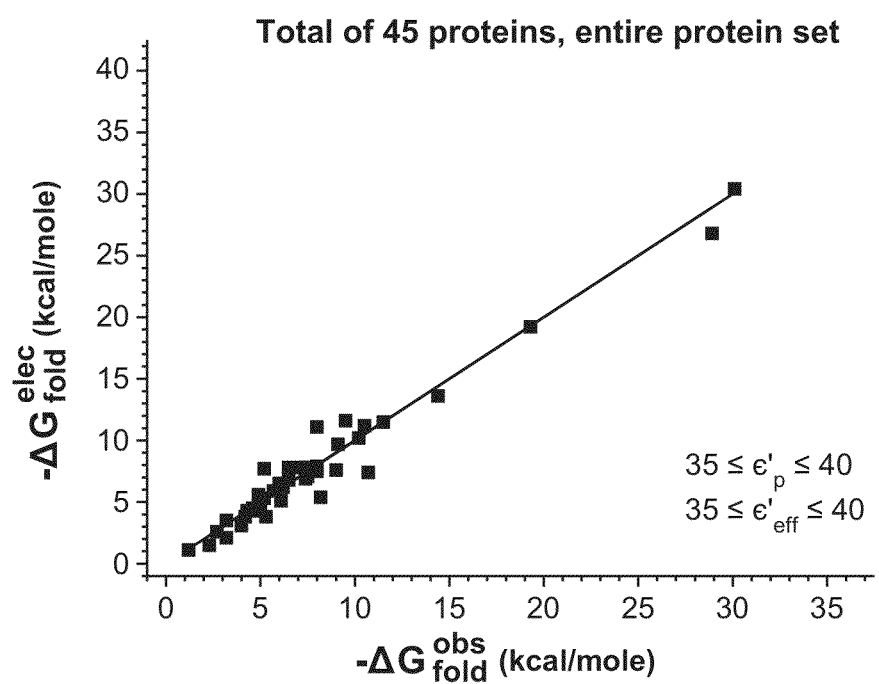
FIG. 7 shows that the folding energy determined by the methods of this disclosure correlates well with the experimentally determined values, based on the 45 training proteins.

This special treatment is rationalized by the fact that Lys residues can move their center quite easily and thus can adjust their interaction with counter ions (see analysis in Cutler et al. (1989) Biochemistry 28:3188-97). Using both the modified $\in'_p$ and $\in'_{eff}$ for Lys allowed this example finally to obtain much better results, as shown in FIG. 7, and in the corresponding columns in Table III. Now the agreement between the best fitted $\Delta G_{fold}^{elec}(\in'_p, \in'_{eff})$ and $\Delta G_{fold}$ is excellent.

TABLE III

Predicted $\Delta G_{fold}$ for the series of proteins considered in this example[a]

| No. | Protein | $-\Delta G_{fold}^{elec}$ | $-\Delta G_{fold}^{obs}$ | \|Error\| | Best $\epsilon_p$ | Best $\epsilon_{eff}$ | $-\overline{DG}_{fold}^{calc}$ | \|Error\| |
|---|---|---|---|---|---|---|---|---|
| 1 | SSO7d | 7.9 | 8.0 | 0.1 | 40 | 40 | 8.5 | 0.5 |
| 2 | Thioredoxin[b] | 4.4 | 9.0 | 4.6 | 40 | 35 | 3.1 | 5.9 |
| 3 | Barstar | 5.9 | 5.7 | 0.2 | 35 | 35 | 4.9 | 0.8 |
| 4 | Apoflavodoxin | 4.3 | 4.3 | 0.0 | 35 | 40 | 5.0 | 0.7 |
| 5 | λ-Repressor | 4.5 | 4.6 | 0.1 | 40 | 40 | 4.8 | 0.2 |
| 6 | Snase | 6.3 | 6.2 | 0.1 | 35 | 40 | 8.0 | 1.8 |
| 7 | BsHpr, Phosphotransferase | 3.1 | 4.0 | 0.9 | 40 | 35 | 2.1 | 1.9 |
| 8 | FeCyt b$_{562}$ | 7.7 | 5.2 | 2.5 | 35 | 40 | 9.7 | 4.5 |
| 9 | Arc Repressor | 4.3 | 4.6 | 0.3 | 40 | 35 | 1.7 | 2.9 |
| 10 | Aspartate Amilotransferase | 26.8 | 28.9 | 2.1 | 40 | 40 | 31.0 | 2.1 |
| 11 | Chey | 11.6 | 9.5 | 2.1 | 35 | 40 | 13.5 | 4.0 |
| 12 | GDH Domain II | 5.6 | 4.9 | 0.7 | 35 | 35 | 4.2 | 0.7 |
| 13 | Histidine Phosphocarrier | 5.4 | 8.2 | 2.8 | 40 | 35 | 4.5 | 3.7 |
| 14 | Phosphotransferase, Histidine containing protein | 5.3 | 5.2 | 0.1 | 40 | 35 | 4.0 | 1.2 |
| 15 | Ribosomal | 7.4 | 10.7 | 3.3 | 40 | 35 | 6.4 | 4.3 |
| 16 | RNase H* | 7.1 | 7.5 | 0.4 | 40 | 35 | 6.5 | 1.0 |
| 17 | Ferridoxin[b] | 3.8 | 9.3 | 5.5 | 40 | 35 | 3.2 | 6.1 |
| 18 | O-Methyl Guanine DNA methyltransferase | 10.2 | 10.2 | 0.0 | 35 | 35 | 9.1 | 1.1 |
| 19 | Sac7d | 7.8 | 7.4 | 0.4 | 40 | 40 | 9.0 | 1.6 |
| 20 | Histone | 7.8 | 7.2 | 0.6 | 40 | 35 | 7.6 | 0.4 |
| 21 | PFRD-XC4 | 2.1 | 3.2 | 1.1 | 40 | 35 | 1.2 | 2.0 |
| 22 | Staphylococcal Nuclease I92K | 1.5 | 2.3 | 0.8 | 40 | 40 | 2.8 | 0.5 |
| 23 | Staphylococcal Nuclease I92E | 3.8 | 4.2 | 0.4 | 40 | 35 | 2.2 | 2 |
| 24 | Staphylococcal Nuclease | 11.5 | 11.5 | 0.0 | 35 | 35 | 10.3 | 1.2 |
| 25 | Bs CSP | 1.1 | 1.2 | 0.1 | 35 | 35 | 0.8 | 0.4 |
| 26 | Bc CSP | 5.2 | 5.0 | 0.2 | 40 | 35 | 4.2 | 0.8 |
| 27 | Tm CSP | 6.8 | 6.5 | 0.3 | 35 | 40 | 8.0 | 1.5 |
| 28 | Ubiquitin D21N | 5.1 | 6.1 | 1.0 | 40 | 35 | 3.9 | 2.2 |
| 29 | Ubiquitin F45W | 6.9 | 7.4 | 0.5 | 40 | 35 | 5.9 | 1.5 |
| 30 | Ubiquitin K27A | 4.3 | 4.4 | 0.1 | 40 | 40 | 4.8 | 0.4 |
| 31 | Tm DHFR | 30.4 | 30.1 | 0.3 | 40 | 35 | 25.9 | 4.2 |
| 32 | Ec DHFR | 6.5 | 6.0 | 0.5 | 35 | 35 | 4.9 | 1.1 |
| 33 | Ribonuclease | 11.2 | 10.5 | 0.7 | 40 | 40 | 13.1 | 2.6 |
| 34 | Glucanase C[b] | 0.0 | 0.0 | 0.0 | — | — | 0.0 | 0.0 |
| 35 | Phospholipid A2 | 7.8 | 6.5 | 1.3 | 35 | 40 | 9.1 | 2.6 |
| 36 | Trypsin Proteinase | 7.7 | 7.5 | 0.2 | 35 | 35 | 6.8 | 0.7 |
| 37 | Interleukin | 9.7 | 9.1 | 0.6 | 35 | 35 | 8.9 | 0.2 |
| 38 | Adhesion transferase Y92E | 7.5 | 8.0 | 0.5 | 40 | 40 | 8.4 | 0.4 |
| 39 | Complement | 2.6 | 2.7 | 0.1 | 35 | 35 | 2.5 | 0.2 |
| 40 | Cytochrome b5 Rat | 3.5 | 3.2 | 0.3 | 35 | 35 | 2.3 | 0.9 |
| 41 | Gene V DNA Binding | 7.6 | 9.0 | 1.4 | 40 | 35 | 6.6 | 2.4 |
| 42 | Glu Transferase | 13.6 | 14.4 | 0.8 | 35 | 35 | 10.2 | 4.2 |
| 43 | Growth Factor | 0.0 | 0.0 | — | — | — | 0.0 | 0.0 |
| 44 | Isomerase | 19.2 | 19.3 | 0.1 | 40 | 35 | 13.7 | 5.6 |
| 45 | Ribosomal S6 | 11.1 | 8.0 | 3.1 | 35 | 40 | 12.9 | 4.9 |

[a]All free energies reported are in kcal/mol. The third column reports the experimental values of the absolute stabilities of the tested proteins. The last two columns give the predicted stability according to Eq. (11) and the corresponding error. The sources of the observed values are given in Table I.
[b]Proteins containing a disulfide bond (which is not treated by the present method) where the corresponding "missing" energy is around 5 kcal/mole.

Figure 4:
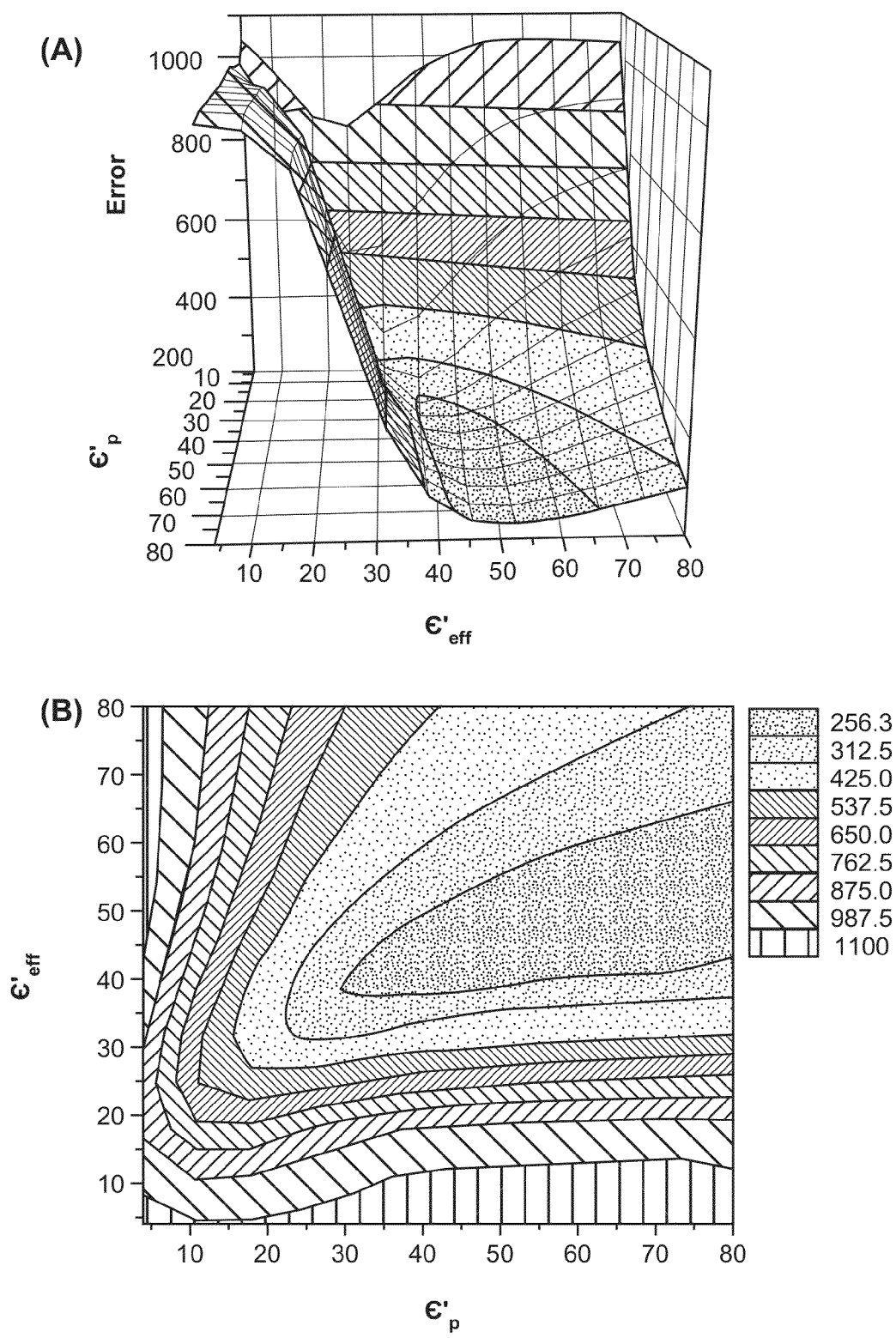
FIG. 4 are the surface (A) and contour plots (B) of $F_{eror}(\in'_p,\in'_{eff})$ which clearly shows that the best fitted values for the dielectric constants follow approximately the line $\in'_p=\in'_{eff}$, and that for $\in'_p=\in'_{eff}=40$ and above where the error reaches its minimum plateau.
Figure 8:
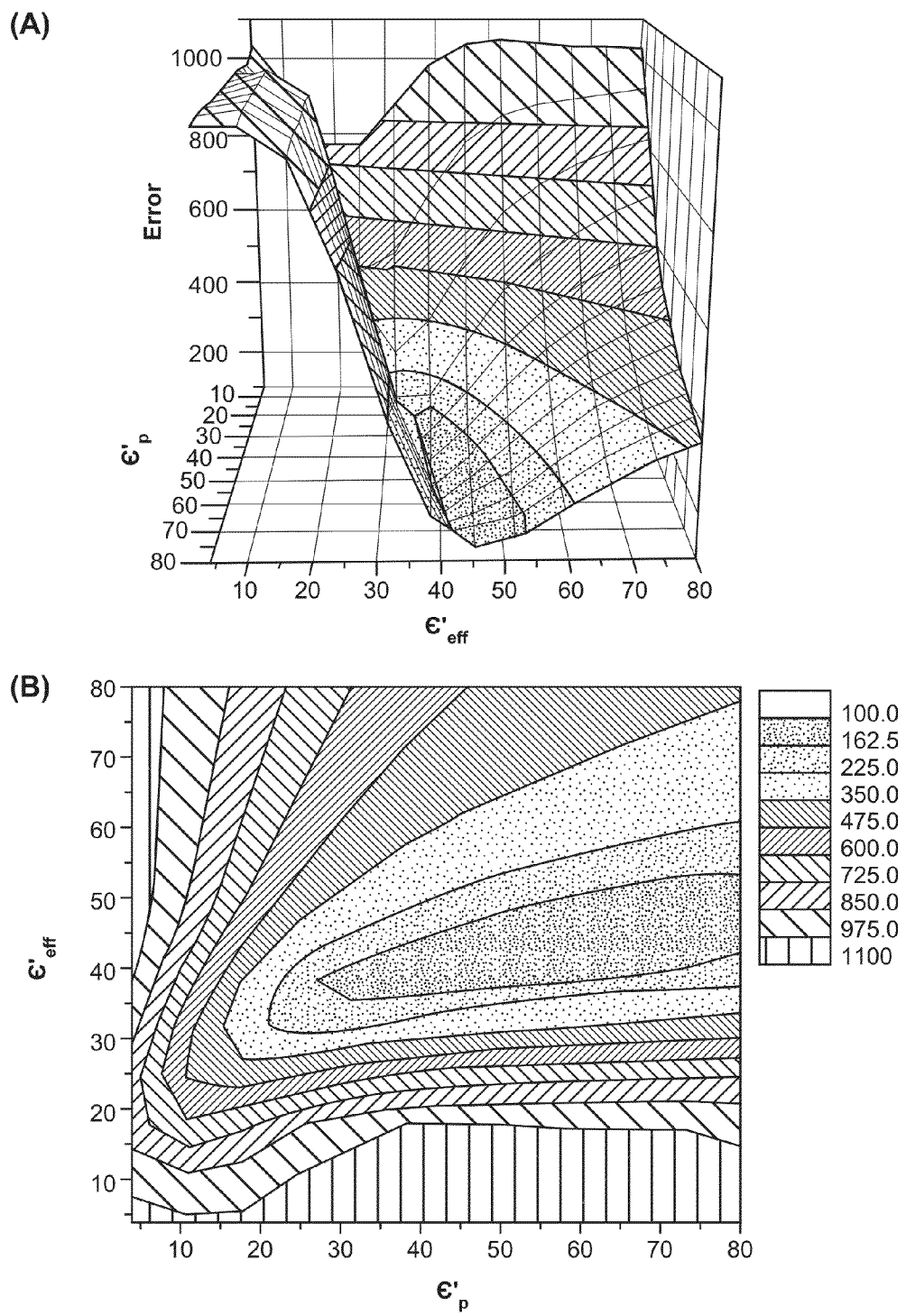
FIG. 8A-B are the surface (A) and contour plots (B) of $F_{eror}(\in'_p,\in'_{eff})$ obtained after refinement of $\in'_p$ for internal groups and $\in'_{eff}$ for Lys; The plots of FIG. 8 show clearly that the best fitted values for the dielectric constants follow approximately the line $\in'_p=\in'_{eff}$, with a global minimum of around $(\in'_p,\in'_{eff})=(40,40)$ which means that values of $\Delta G_{fold}^{elec}(\in'_p, \in'_{\mathit{eff}})$ proximal to $\Delta G_{fold}$ can be acquired when $\in'_p, \in'_{\mathit{eff}}$ have high values, and $\in'_p = \in'_{\mathit{eff}}$.

Using the results described in FIG. 7 to calculate the sum of errors $F_{error}(\in'_p, \in'_{eff})$ introduced in Eq. (7), this example evaluated again the best fitted values for the dielectric constants by determining the region of $(\in'_p, \in'_{eff})$ where $F_{error}(\in'_p, \in'_{eff})$ is minimized. This treatment led to the surface described in FIGS. 8(A) and 8(B). The best fitted region follows again an approximate line where $\in'_p = \in'_{eff}$. The main difference between FIGS. 4 and 8 is that the region with $\in'_p = \in'_{eff}$ corresponds to much deeper valley (indicating a minimum in the function $F_{error}(\in'_p, \in'_{eff})$).

Table III summarizes the calculated results for the best fitted dielectric constants. As seen from Table III, this example obtained quite accurate results. Most of the protein tested show error of around 1 kcal/mole, and only a few have errors above 2 kcal/mole, while still not exceeding 3 kcal/mole. The average error for the best fitted values of $\Delta G_{fold}^{elec}(\in'_p, \in'_{eff})$ (shown on the forth column of Table III) is only 0.7 kcal/mole.

The $\Delta G_{fold}$ values reported in Table III for Glucanase C is zero, since the protein is unstable according to Creagh et al. (1998) Biochemistry 37:3529-3537. In this case, it is found experimentally that without the Cys6-Cys27 disulfide bond, the protein is unstable, thus this finding that $\Delta G_{fold}^{elec}(\in_p, \in'_{eff})$ is positive for all dielectric constants, is consistent with the experimental observation, since the calculations do not include the disulfide bond. Protein acidic fibroblast growth factor is also unstable under physiological conditions. It is reported that the protein without certain polyanions, remains relatively unstable (Copeland et al. (1991) Arch. Biochem. Biophys. 289:53-61 and Gospodarowicz et al. (1986) J. Cell Physiol. 128:475-84).

Concerning the two proteins of Thioredoxin and Ferridoxin, this method underestimated the observed stability by 5 kcal/mole. However, those two proteins contain one disulfide bond, and since a disulfide bond stabilizes a protein with an amount of approximately 5 kcal/mole, this method is successful in predicting their absolute stabilities.

Predicting Absolute Stabilities of Proteins

This work so far has shown that the calculated absolute stability of a protein can be correlated quite accurately with the corresponding observed value, by choosing best fitted values of $\in_p$ and $\in'_{eff}$ in the region $35 \le \in_p \le 40$; $35 \le \in'_{eff} \le 40$.

This however is not fully unbiased since the "best fitted" values are taken as the values that give the best result.

Thus, it is important to select a well defined scheme for actually predicting the relevant stability. After considering several options, this example concluded that a reasonable prediction can be obtained by using:

$$\overline{\Delta G_{fold}^{calc}} = \frac{\Delta G_{fold}^{elec}(35, 35) + \Delta G_{fold}^{elec}(35, 40)}{4} + \frac{\Delta G_{fold}^{elec}(40, 35) + \Delta G_{fold}^{elec}(40, 40)}{4} \quad (11)$$

Figure 9:
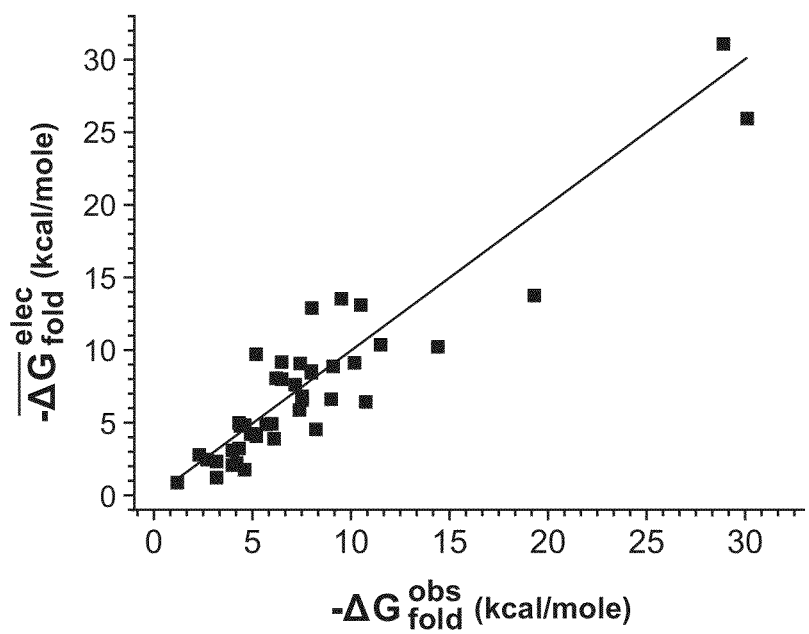
FIG. 9 shows calculated and observed folding energies in which the calculations were done using Eq. (11), rather than by choosing the best fitted values of $\Delta G_{fold}^{elec}(\in'_p, \in'_{\mathit{eff}})$, as was in FIG. 7.

The corresponding result for $\overline{\Delta G_{fold}}^{calc}$ are shown on the right columns of Table III and in FIG. 9. As seen from the figure, the agreement is reasonable (an average error of 1.8 kcal/mole) although less impressive than that of FIG. 7. However, in this case, this example is not selecting any best fitted values and shows a robust way of predicting protein stability.

Dependence of Absolute Stabilities on the Size and Fold of the Protein

During the validation of the model this example examined the possible influence/dependence of factors such as protein size and fold on absolute stability. To investigate such dependence, this example chose the protein test set that included proteins of largely different size and fold. Comparisons of both the observed and the calculated stability with size and fold of proteins didn't show any particular correlation. For example, there are many small proteins in the test set shown in Table I, which have relatively large values of observed and calculated absolute stabilities (for example SSO7D, Histidine Phosphocarrier and Sac7d) but at the same time there are many that show low values (for example Barstar, PFRD-X64, and Bs CSP). The same trend is observed for large proteins (for example staphylococcal nuclease, isomerase, Tm DHFR, and aspartate amilotransferase show large values of absolute stability, while GDH Domain II, staphylococcal nuclease I92K, and Ec DHFR have low values for absolute stability). Comparison of fold and absolute stability also has not showed any correlation, i.e., whether the structures were mainly alpha, mainly beta, amorphous, or alphabeta, didn't show an important difference in absolute stability.

Finally, no correlation between best fitted values of $\in_p$ and $\in'_{eff}$ and the size or fold has been observed.

A Practical and Powerful Approach for Stabilizing Proteins

The present approach provides a powerful new way of stabilizing proteins by systematic mutations. One can just use Eq. 6 and examine systematically different mutant. Another effective approach is obtained by differentiating Eq. 6 and evaluating the gradient of the free energy with regards to the charges of the protein residues.

$$\frac{\partial \Delta G_{fold}^{elec}}{\partial Q_i} \approx -2.3RT(pK_{i,int}^p(\varepsilon'_p) - pK_{i,w}^w) + 332 \sum_{i \ne j} Q_j \left[ \frac{1}{r_{ij}(\varepsilon'_{eff})_{ij}} \right] \quad (12)$$

The gradient can then be used in predicting the change of charges that will stabilize the protein, using $$\Delta Q_i = -\alpha \left( \frac{\partial \Delta G_{fold}^{elec}}{\partial Q_i} \right) \quad (13)$$

Determining mutations that would lead to the largest stability of the given protein can be done using the gradient of the folding free energy with respect to the charge of each of the protein residues. The gradient provides the predicted change in charge ($\Delta Q_i$) for each residue. When the predicted change of charge is positive, it means that changing the protein residue to a more positively charged residue, e.g., changing to a positively charged residue if the original residue is neutral, or changing to a neutral residue if the original residue is negatively charged, will increase the protein stability. If the predicted charge in change ($\Delta Q_i$) is negative it means that changing the residue to a more negatively charged residue, e.g., changing to a negative residue if the original residue is neutral, or changing to a neutral residue if the original residue is positively charged, will increase the protein stability.

EXAMPLE 2

This example takes a previously designed kemp eliminases to demonstrate how the method of the present disclosure is used in designing stable and active proteins. The observed absolute catalytic effect and the effect of directed evolution are reproduced and analyzed. It is found that, in the case of kemp eliminase, the transition state charge distribution makes it hard to exploit the active site polarity, even with the ability to quantify the effect of different mutations. Unexpectedly, it is found that the directed evolution mutants lead to the reduction of solvation of the reactant state by water molecules rather that to the more common mode of transition state stabilization used by naturally evolved enzymes.

This example also shows that, contrary to the method of the current disclosure, transition state (TS) stabilization by delocalization effects, as proposed by Rothlisberger et al. (2008) Nature 453:190-195, is unlikely to provide a significant catalytic factor since the same effect exists in the reference solution reaction.

At present there are still many who believe in dynamical and other esoteric effects that are presumed to contribute to catalysis (for review see Kamerlin and Warshel (2010) Proteins 78:1339-75). In many cases it is clearly suggested that improving such effects will be crucial for optimal enzyme design (e.g., Nagel and Klinman (2009) Nat. Chem. Biol. 5:543-50). However, it is shown here that by far the main factor that actually contributes to catalysis is the preorganization effect and thus there is no rational way for improving dynamics and related effects as these factors do not contribute to catalysis (Kamerlin and Warshel (2010) Proteins 78:1339-75). It is also noted that factors such as pi-stacking stabilization are unlikely to be effective in providing significant TS stabilization, beyond the simple effect of induced dipoles. Thus the focus should be placed on the refining of the polar reorganization, as this example attempted to do.

Therefore, this example has demonstrated the ability to reproduce quantitatively the absolute catalytic effects and mutational effects in naturally evolved enzymes and in designer enzymes. This clearly indicates that the catalytic power of enzyme is not due to elusive effects (e.g., conformational dynamics), but to what is by now well understood; the electrostatic preorganization. Thus the difficulties in improving designer enzymes are not due to overlooking misunderstood factors, but to the difficulties in optimizing well understood factors. In other words, a method that reproduces the catalytic rate in known systems should be able to do so in any unknown sequence and the challenge is to find the unknown optimal sequence. The present study provides a useful analysis of the reasons for the less that perfect performance of current designer enzymes.

Further details of this example are provided in the Applicants' article, Frushicheva et al. (2010) "Exploring challenges in rational enzyme design by simulating the catalysis in artificial kemp eliminase," Proc. Natl. Acad. Sci. USA 2010 Sep. 9. [Epub ahead of print], the content of which is incorporated into the current disclosure in its entirety by reference.

Methods

The free energy surface of the reference solution reaction was estimated by ab initio calculations, in the same way described in Kamerlin and Warshel (2009) J. Phys. Chem. B 113:15692-8. In converting the ab initio results to the corresponding EVB this example takes into account the complex nature of the reaction with a concerted proton transfer and C—N bond breaking. Usually this requires three diabatic states, but this example uses two states with modified charges that reproduce the ab initio TS charges. The EVB calculations were carried by MOLARIS simulation program (Lee et al. (1993) J. Comput. Chem. 14:161-18) using the ENZYMIX force field. The EVB activation barriers were calculated at the configurations selected by the free energy perturbation umbrella sampling (FEP/US) approach. The simulation systems were solvated by the surface constrained all atom solvent (SCAAS) model (Lee et al. (1993) J. Comput. Chem. 14:161-18) using a water sphere of 18 Å radius centered on the substrate and surrounded by 2 Å grid of langevin dipoles and then by a bulk solvent, while long-range electrostatic effects were treated by the local reaction field (LRF) method (Lee et al. (1993) J. Comput. Chem. 14:161-18). The EVB region is consisted of the substrate and the carboxylic group of the glutamic amino acid that serves as a proton acceptor. Validation studies were done within 22 Å radius of inner sphere. The FEP mapping was evaluated by 21 frames of 20 ps each for moving along the reaction coordinate using SCAAS model. All the simulations were done at 300 K with a time step of 1fs. In order to obtain reliable results the simulations were repeated 20 times with different initial conditions (obtained from arbitrary points in the relaxation trajectory). The mutant systems were generated from the native enzymes via 100 ps relaxation runs.

Results

Rational enzyme design is expected to have a great potential in industrial application and eventually in medicine. Furthermore, the ability to design efficient enzymes might be considered as the best manifestation of a true understanding of enzyme catalysis. However, at present there has been a limited success in most attempts of rational enzyme design, and the resulting constructs have been much less effective than the corresponding natural enzymes. Furthermore, despite the progress in directed evolution, this field does not have unique rationales for the resulting rate enhancements.

Most attempts to identify the problems with the current rational design approaches have not been based on actual simulations of the given effect. In fact, it has been argued, that the problems are due to the incomplete modeling of the transition state (TS) and to the limited awareness to the key role of the reorganization energy. Even a recent attempt to use a molecular orbital-combined quantum mechanical/Molecular mechanics (MO-QM/MM) approach has not provided a reasonable estimate of the observed catalytic effect or the trend of the mutational effects in an artificially design enzyme. Thus, reproducing the effect of directed evolution and eventually obtaining better performance in enzyme design, are crucial for understanding what is exactly missing in current approaches.

Semiquantiative computational studies of the effect of mutations on enzyme catalysis date back to the empirical valence bond (EVB) simulations of the anticatlytic effect of mutations of trypsin. Subsequent calculations of known and predicted mutational effect include EVB studies and more recent (MO-QM/MM) studies. The above studies, and in particular the quantitative one, have established the importance of the changes in reorganization energy upon mutations. Recent study has explored the ability of the EVB approach to be used in quantitative screening of design proposals. However, such approaches have not been used in actual predictive design studies, and the applicants are not aware of any study that used the ability to determine activation barriers quantitatively as a successful guide in subsequent enzyme design experiments.

It is found that it is not extremely difficult to use the EVB to reproduce the overall catalytic effect or to suggest mutations with large anticatlytic effect that will reduce the overall catalysis. This was demonstrated in several enzymes. However, it is much harder to suggest mutations that will drastically increase catalysis. Thus this example tried to explore this challenge and chose as a test system the Kemp elimination reaction (Kemp and Casey (1973) J. Am. Chem. Soc. 95:6670-80). The design of enzymes that catalyze this reaction has been the center of recent excitements (Debler et al. (2005) Proc. Natl. Acad. Sci. USA 102:4984-9 and Rothlisberger et al. (2008) Nature 453:190-195.), but as will be argued below the design has not obtained effective transition state stabilization. This example focused on both validation of the power of the EVB and more importantly on exploring the effect of the directed evolution and on the requirement for improving the catalysis of the previously designed enzymes.

1. Systems

Figure 11:
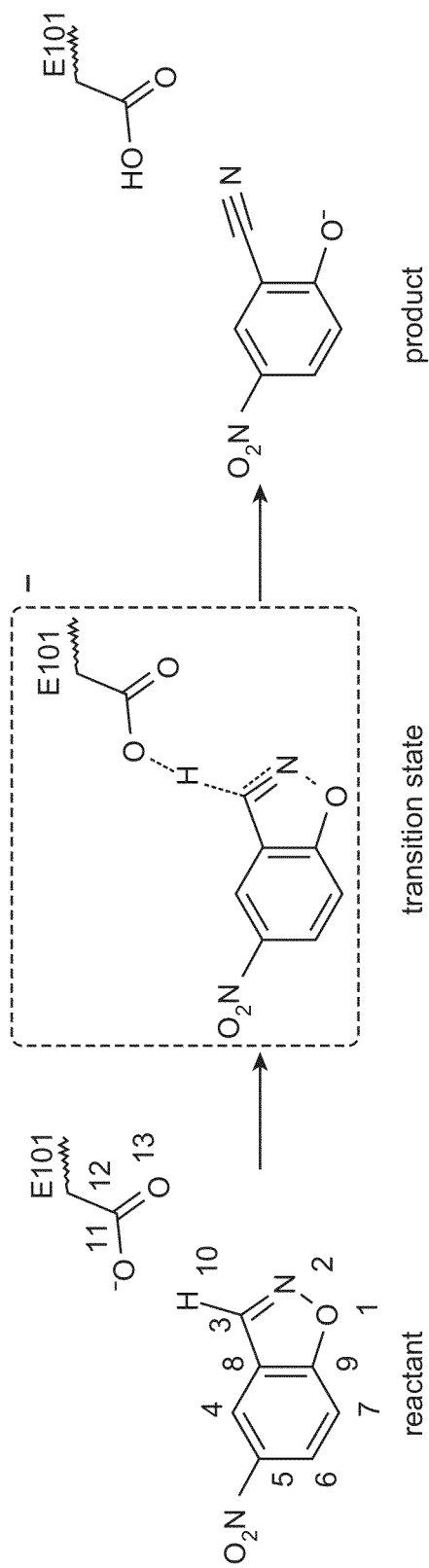
FIG. 11 is a schematic description of the kemp elimination reaction.

The system chosen as a benchmark for the present study is the Kemp elimination reaction (Kemp and Casey (1973) J. Am. Chem. Soc. 95: 6670-80) of 5-nitrobenzioxazole with a carboxylic acid as a base (FIG. 11). In order to explore the catalysis in this system this example quantified first the energetics of the reaction in water (Warshel et al. (2006) Chem. Rev. 106, 3210-3235). Here one may try to use the rate constant of the uncatalyzed reaction in water ($1.2 \cdot 10^{-6} M^{-1} s^{-1}$ at pH=7.25), but this reaction involves a large contribution from the hydroxide ion OH⁻ available at this pH. Furthermore, it is much more useful and relevant to consider the "chemically filtered" reference reaction, which is defined as the solution reaction that follows exactly the same mechanism as the one in the enzyme. The corresponding rate constant was determined by taking the estimate of the rate of the reaction of 5-nitrobenzioxazole in acetate buffer ($5 \cdot 10^{-5}$ $M^{-1}s^{-1}$) and extrapolating it to 55M to obtain the rate constant ($k_{cage}$) of 0.0025 $s^{-1}$, for the case when the donor and acceptor (the substrate and a carboxylic acid) are placed at the same solvent cage. Similar conclusions were obtained by other estimates, including ab initio calculations. The relevant activation barrier is given in Table IV. It is noted that this example is not talking on $k_{cat}/K_M$ relative to the uncatlyzed reaction, where the effect of the enzyme is larger, since this rate enhancement includes the effect of binding to the active site and the real challenge is to optimize $k_{cat}$.

TABLE IV

The $\Delta g_{cat}^{\ddagger}{}_p$ for the systems explored in this example[a].

| System: | $\Delta g^{\ddagger}_{obs}$, kcal/mol | $\Delta g^{\ddagger}_{calc}$, kcal/mol |
|---|---|---|
| Water (cage) | 21.2 | 21.1 |
| KE07 (wt, PDB: 2RKX) | 20.1 | (20.2) 19.5 |
| KE07 (wt, PDB: 2RKX) + H2O | 20.1 | 20.4 |
| R6 3/7 F (PDB: 3IIP) | 17.8 | 16.1 |
| R7 2/5 B (from R6 3/7F) | 17.6 | 18.0 |
| A9S (from wt) | 20.1 | (17.2) 19.3 |
| A9N (from wt) | 20.1 | (17.5) 19.5 |
| A9T (from wt) | 20.1 | 21.6 |

[a]In brackets the results with the qualitative charge set (set B) while all other results correspond to the quantitative set (set A).

Interestingly, the reference reaction in a solvent cage is not much slower than the reaction catalyzed by the originally designed enzyme ($k_{cat}$=0.02-0.3 $s^{-1}$) (see (Rothlisberger et al. (2008) Nature 453:190-195)). This indicates that a major part of the catalytic effect is due to just placing the donor and acceptor in a contact distance.

2. Validation on Existing Constructs

Figure 12:
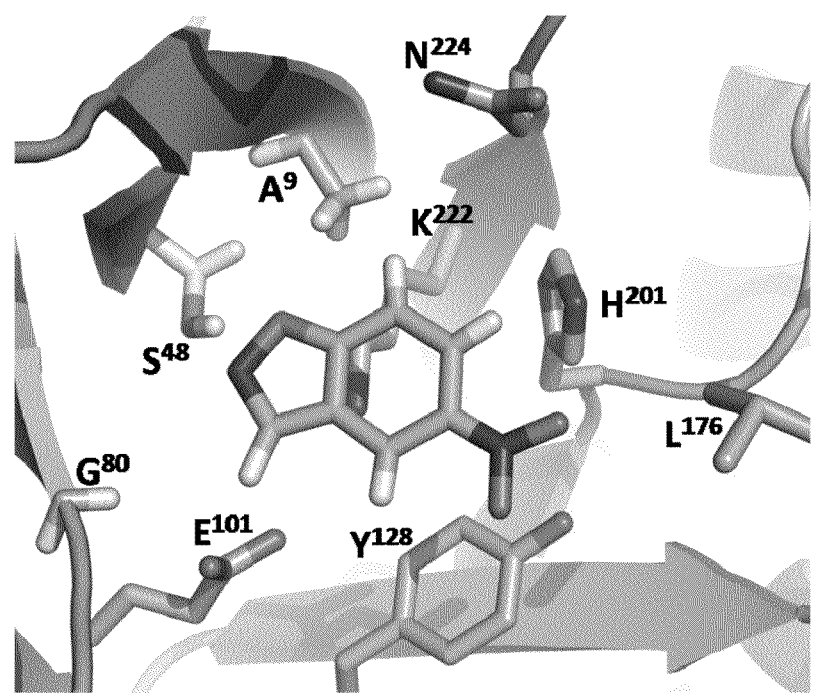
FIG. 12 illustrates the structure of the native enzyme (PDB: 2RKX) with the docked substrate.
Figure 13:
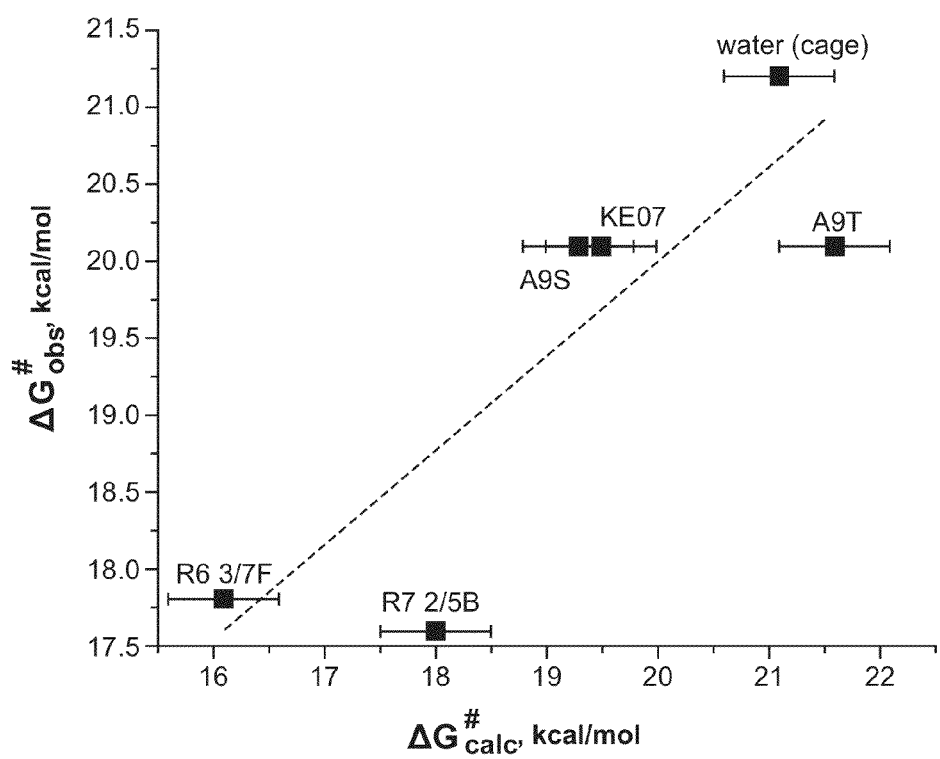
FIG. 13 shows correlation between the calculated and observed activation barriers.

In order to validate the EVB approach this example started by trying to reproduce the observed $k_{cat}$. This was done by calibrating an EVB surface for the reaction in solution (by forcing it to reproduce the observed activation barrier and calculated exothermicity) and using the calibrated EVB parameters in studies of the reaction in the protein. The initial structures of the "native" and mutant proteins were taken from the corresponding X-ray structures. The reacting substrate was placed in each active site in a similar orientation to that in the design KE07 model and relaxed. The resulting orientations (e.g., FIG. 12) are similar to those in the original design. Twenty structures were saved during each relaxation process, and then used to generate the EVB surface and obtain the activation free energies. As seen from the table the calculated and observed catalytic effects are in good agreement with each other.

One of the interesting results of the analysis is the finding that the initial design (KE07) has not lead to significant rate enhancement above that effect expected from placing the acid and the base at the same cage (see Table IV).

3. Initial Screening

In order to obtain an improved rational design it is crucial to be able to explore the dependence of the TS energy on each residue. Since the electrostatic effect is by far the most important factor in enzyme catalysis, this example started with an attempt to estimate the electrostatic contributions expected from each residue. This was done by evaluating the effect of changing the substrate charges (upon moving from the RS to the TS) on the contribution of each residue. More specifically this example assigned (artificially) to each protein residues a charge of +1 and then calculated the change in the corresponding "group contribution" when the residual charges (or polarity) of the reacting substrate changes. The change, $\Delta G_i$, is then used to estimate the optimal change in the charges (or polarity) of the protein residues and thus the optimal mutations.

The approach is based on the realization that the electrostatic contributions of the protein residues to the activation barrier can be very roughly approximated by:

$$\Delta \Delta g_{elec}^{\ddagger} \cong 332 \sum_{ij} \sum_{k} (q_j^k \Delta Q_i)/r_{ij}\varepsilon_{ij} \quad (1')$$

where $q_j^k$ are the residual charges of the protein atom, j runs over the protein residues and i over the substrate atoms, $\varepsilon_{ij}$ is the dielectric constant for the specific interaction. The $\Delta Q_i$ are the changes in the substrate charges upon going from the RS to the TS.

Figure 14:
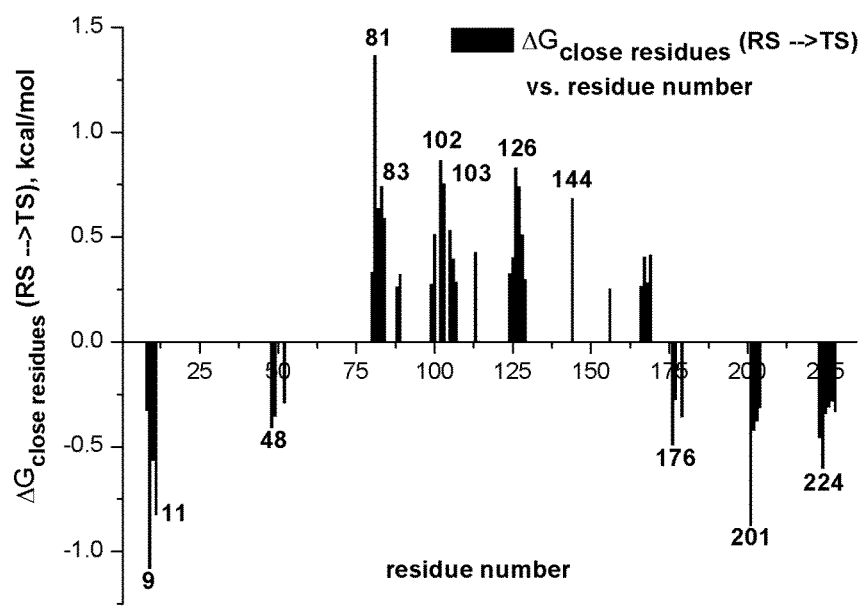
FIG. 14 shows the group contributions (in kcal/mol) that reflect the interactions between the protein residues with the charge change upon moving from the reactant state (RS) to the transition state (TS) ($\Delta Q$ in Eq. 9) where the calculations are done with $\in_{ij}=4$ for all residues and the largest negative contributions provide a rough guide for the optimal sites for effective mutations that will enhance the catalytic effect.

Eq. 1' can be used for estimating the most effective charge changes in each site and this was done in examining the trend with two charge sets (set B that used the ab initio RS and PS as the corresponding EVB charges for the RS and PS, and a much more rigorous set (set A), that forced the EVB TS charges to reproduce the ab initio TS charges. The resulting group contribution for set A is given in FIG. 14. It appears that the TS charges in the Kemp elimination reaction do not follow a simple rule of Set B (being the average of the RS and PS charges) and apparently the charge change on O1 is unexpectedly small.

Figure 15:
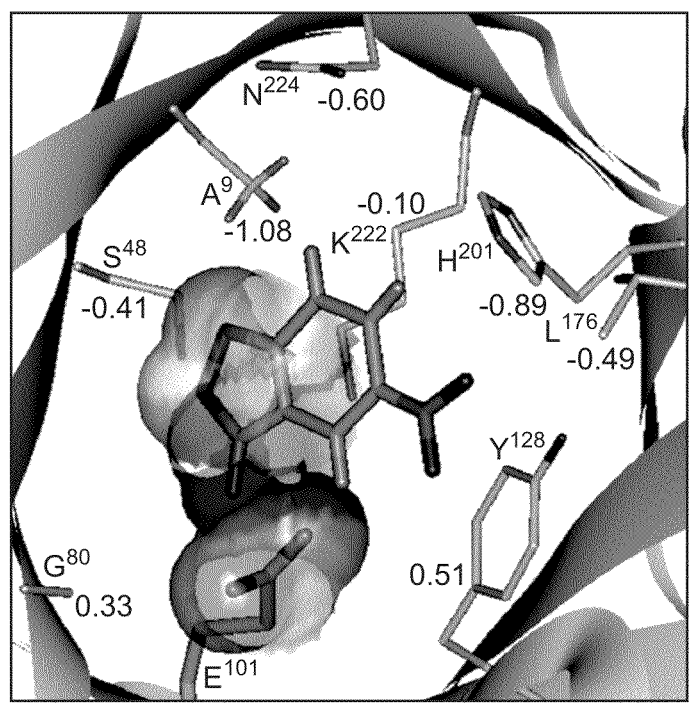
FIG. 15 shows that the electrostatic potential form the change of the substrate charges upon moving from the RS to the TS (red and blue for negative and positive potential respectively) and group contributions (in kcal/mol) of key residues, where the contributions are defined for the case where each residue is positively charged; and, FIG. 16 shows the water penetration near Glu101 in the wildtype (A) and the R63/7F mutant (B) and there are fewer water molecules near Glu101 in the mutant.

It is instructive to examine the potential due to the $\Delta Q_i$ of each of the atoms of the reacting system, and the corresponding group contributions. These features, which are depicted in FIG. 15 suggest that the TS may be stabilized by placing a positive charge or a hydrogen bond near the regions were the negative charge is developing during the proton transfer process. There is also an option to stabilize the positive charge developing on Glu101. This can be also done by destabilizing the reactant charge. Unfortunately, the group contributions are quite small in the case of the Kemp elimination reaction and do not provide a clear hint for a mutation with a large effect (see below).

4. Analysis of Suggested Mutations

Trying to exploit the hints from the calculated group contributions this example examined first the intuitive hints of the qualitative TS charge set (Set B) performing EVB calculations, with set B, of mutations that would change residue 9 to polar residues and provide stabilization of the charges that might develop on O1. The Initial calculated increase in TS stabilization for the mutations is given in bracket in Table IV.

As seen from the table the A9S mutant (with the qualitative set B) is predicted to increase the catalytic effect.

Instructively, the effect of the A9S and A9N mutations was explored recently and these mutations did not lead to any catalytic improvement (see Table IV), in an apparent contrast to the trend predicted by set B charges and to simple qualitative considerations. Thus this example looked for pitfalls, starting with the possibility of having a water molecule in the space between Ala 9 and O1. However, the calculations (with set A) produced small and inconclusive effect, and the use of the set B could not rationalize the lack of detectable effect of polar groups on the supposedly developing TS charge of O1. Thus this example considered the fact that the TS charges cannot be represented by the intuitive set and this example moved to the more realistic (and non intuitive) set A. Now this example obtained the results listed in Table IV (without brackets) where almost all the predicted effect of polar stabilization of the O1 developing charge disappeared. This learning process provided an interesting example where mutational effect forces one to look more carefully at the theoretical model.

Considering the difficulties in obtaining a major effect by improving the active site polarity, this example looked for possible hints from the directed evolution experiments (here it focused on R6 3/7 F). The starting point was the fact that this example succeed, for the first time, to reproduced computationally the observed effect and thus have the tools to examine its origin. It was found that the mutant has an early TS, due to both small destabilization of the reactant state and stabilization of the product state. Apparently, while the water molecules play an important role in the wt, they provide less solvation of the reactant state charges of the mutant (see FIG. 6). However, even the directed evolution did not find a major way of TS stabilization (see below).

5. What can be Learned from Related Systems

Figure 16:
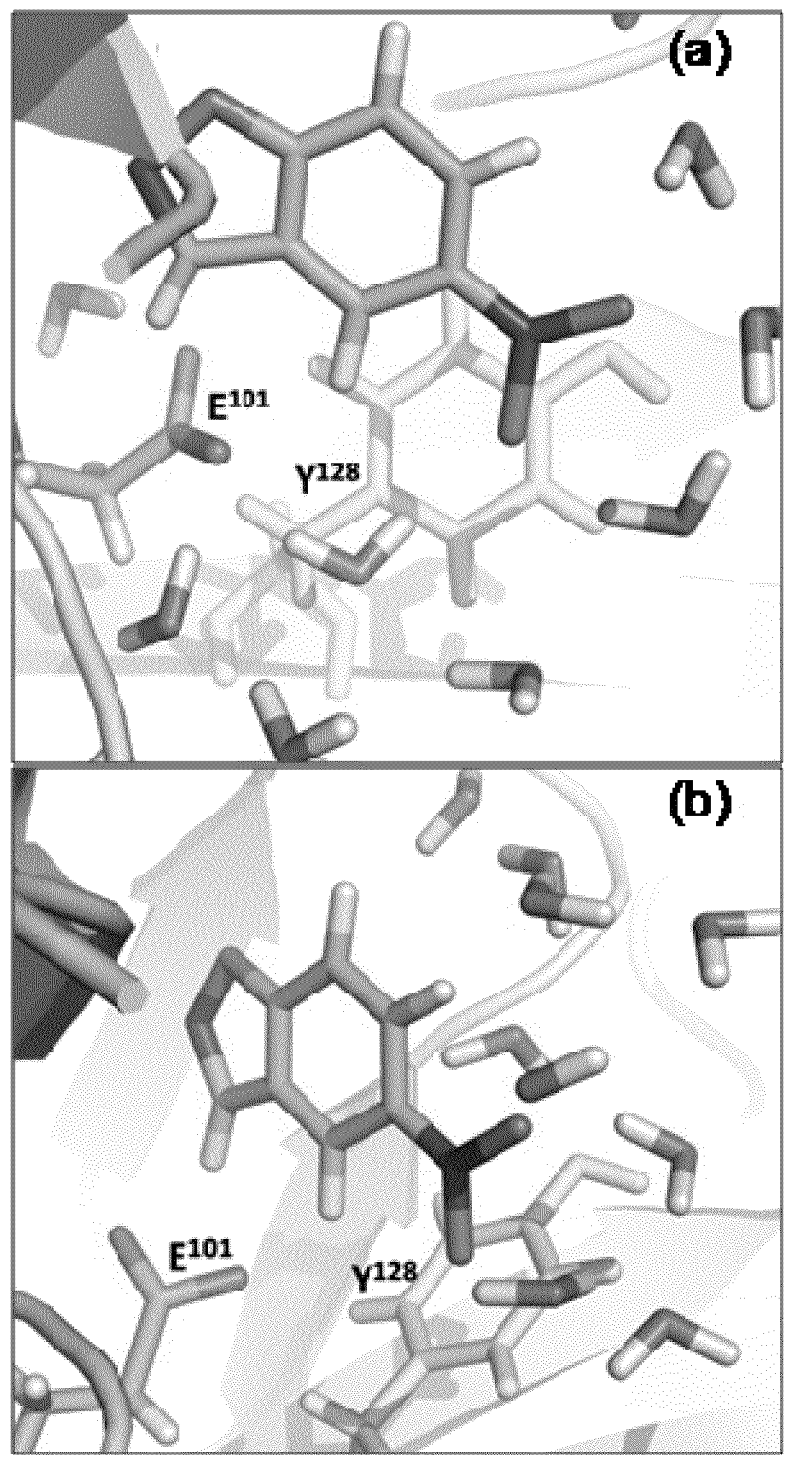

The Kemp elimination reaction is formally similar to other reactions where a negative charge is being transfer from the ionized acid to the substrate. A good example is the reaction of haloalkan dehalogenase (DhlA), where there is a negatively charged Asp group in the RS [(−) (0)] configuration transfers its negative charge to a leaving group (Cl) and form a [(−½) (−½)] configuration in the TS (here the first and second bracket correspond to the charge on Asp and on the Cl atom). In this case it was shown by quantitative LRA analysis (Olsson and Warshel (2004) J. Am. Chem. Soc. 126:15167-15179) that, while in solution the system lose a very large solvation energy upon moving to the TS, in the enzyme the loss of solvation energy is much smaller, resulting in a major TS stabilization (relative to the solution reaction). This is accomplished by the preorganization of two polar hydrogen bonds (Trp125 and Trp175) that stabilizes the −½ charge of the living Cl atom. Unfortunately, in the case of the Kemp elimination, the charge that is being transferred to the substrate is much more delocalized and thus making possible the preorganization effects less effective. Here it seems that the solution found by the directed evolution involves reducing the solvation of the reactant state by water molecules. This does not involve significant reactant state destabilization since $K_M$ increases by only factor of 3 (which means that the binding energy is similar for the native and mutant enzyme). However, the destabilization of the ionized Glu101 chosen here can also be consider as a reactant state destabilization (RSD) effect, but it is clearly not the standard avenue chosen by DhlA and other naturally evolved enzymes (see systematic analysis in table S2). Perhaps, the problem is the ability of the water molecules to approach the proton donor (see FIG. 16). Here a change of the enzyme scaffold to block entrance of water molecules near Glu101 can be useful. Perhaps replacing Asn103 by a larger residue will be effective in improving the wildtype enzyme.

6. Prospect for Computer Aided Directed Evolution

Applicants have indicated that the effect of ionized residues at a distance of more than 6 Å can be approximated by using a relatively large effective dielectric constant for charge—charge interaction. Here one can obtain rather reliable prediction for the effect of ionized residues. Apparently a preliminary experimental screening seems to be consistent with the prediction. However, only actual evaluation of $k_{cat}$ will provide a validation of these predictions. Furthermore, unfortunately the dipole generated by the $\Delta Q_i$ is relatively small and is not predicted to give substantial interaction with distanced ionized residues. Perhaps using the KE70 mutants where the proton acceptor is histidine can lead to a larger dipole effect.

A further constraint on the design can be imposed by introducing mutations that compensate for the loss of stability during the refinement process. This can be done by the recent focused dielectric approach and the resulting optimized $q_j$, under the constraint of large folding energy, is:

$$(\Delta \bar{q}_j) \approx -\partial G_{fold}/\partial \bar{q}_j - a\partial \Delta \Delta g_{elec}''/\partial \bar{q}_j \qquad (2')$$

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for identifying a substitute amino acid at each of one or more amino acid residues of a reference protein or reference oligopeptide that increases the stability of the reference protein or reference oligopeptide in a custom computing apparatus, wherein the custom computing apparatus comprises at least one processor and a memory, and wherein the method comprises:

receiving, in the memory, a plurality of parameters comprising an intrinsic $pK_a$ of each of the amino acids in the reference protein or the reference oligopeptide, a charge of each of the amino acids in the reference protein or the reference oligopeptide, distances between the amino acids in the reference protein or the reference oligopeptide, a dielectric constant for self-energy ($\in'_p$) which is in a range of 35 to 40 and a dielectric constant for charge-charge interaction ($\in'_{eff}$) which is in a range of 35 to 40;

accessing, by the at least one processor, the plurality of parameters;

calculating, by the at least one processor, a gradient of free energy over charges of a plurality of amino acid residues of a protein or oligopeptide wherein the protein is or oligopeptide initially the reference protein or oligopeptide respectively, and wherein the gradient of free energy over the charges is determined as:

$$\frac{\partial \Delta G^{elec}_{fold}}{\partial Q_i} \approx -2.3RT(pK^p_{i,int}(\varepsilon'_p) - pK^w_{i,w}) + 332\sum_{i\neq j} Q_j\left[\frac{1}{r_{ij}(\varepsilon'_{eff})_{ij}}\right],$$

wherein α is a scaling factor,
($\in'_p$) is a dielectric constant for self-energy,
($\in'_{eff}$) is a dielectric constant for charge-charge interaction, $Q_i$ and $Q_j$ are the charges of the $i^{th}$ and $j^{th}$ residues respectively, $pK_{i,w}^{w}$ is the $pK_a$ of the $i^{th}$ residue in water, $pK_{i,int}^{P}(\in'_p)$ is the intrinsic $pK_a$ of the $i^{th}$ residue in its given protein state when all other residues are neutral, the notation $\in'_p$ indicating that this pKa is a function of $\in'_p$), j is the number of amino acid residues of the protein or oligopeptide, and $r_{ij}$ is the distance between residues i and j;

determining, from the gradient, a change in charge ($\Delta Q_i$) of the protein that increases the stability of the reference protein or reference oligopeptide, wherein the plurality of amino acid residues of the protein or oligopeptide that increases the stability of the reference protein or oligopeptide comprise one or more substitute amino acids as compared to the reference protein or reference oligopeptide, respectively;

repeating the determining the change in charge of the protein that increases the stability of the reference protein or reference oligopeptide to identify substitutions that further stabilize the protein or oligopeptide; and identifying a substitute amino acid at each of one or more amino acid residues of the reference protein or reference oligopeptide that increases the stability by changing the $\Delta Q_i$.

2. The method of claim 1, wherein the $\Delta Q_i$ is determined as: $\Delta Q_i = -\alpha(\delta\Delta G_{fold}^{elec}/\delta Q_2)$.

3. The method of claim 1, wherein the $\in'_p$ for an amino acid residue that is internal to the reference protein or oligopeptide is smaller than the $\in'_p$ for amino acid residues that are not internal to the reference protein or reference oligopeptide, respectively.

4. The method of claim 1, wherein the $\in'_{eff}$ for a lysine residue is smaller than the $\in'_{eff}$ for non-lysine amino acid residues.

5. The method of claim 1, further comprising producing, in a sample, a mutant protein or oligopeptide that comprises the identified substitute amino acid.

6. The method of claim 1, wherein the change in charge of the protein is approximated in increments of +1, −1, or zero.

* * * * *